United States Patent
Boone, III et al.

(10) Patent No.: US 9,918,727 B1
(45) Date of Patent: Mar. 20, 2018

(54) SKIN TREATMENT SYSTEM WITH ADJUSTABLE HEIGHT WAND

(71) Applicant: Envy Medical, Inc., Westlake Village, CA (US)

(72) Inventors: N. Brendon Boone, III, Encino, CA (US); Basil M. Hantash, E. Palo Alto, CA (US); Kenneth B. Karasiuk, Oak Park, CA (US); Steven E. Wojcik, Mukilteo, WA (US)

(73) Assignee: Envy Medical, Inc., Westlake Village, CA (US)

(*) Notice: Subject to any disclaimer, the term of this patent is extended or adjusted under 35 U.S.C. 154(b) by 184 days.

(21) Appl. No.: 14/733,877

(22) Filed: Jun. 8, 2015

Related U.S. Application Data

(62) Division of application No. 12/645,210, filed on Dec. 22, 2009, now Pat. No. 9,050,133.

(51) Int. Cl.
  *A61B 17/22* (2006.01)
  *A61B 17/50* (2006.01)
  *A61B 17/3205* (2006.01)
  *A61B 17/00* (2006.01)
  *A61B 17/32* (2006.01)

(52) U.S. Cl.
  CPC .......... *A61B 17/22* (2013.01); *A61B 17/3205* (2013.01); *A61B 17/50* (2013.01); *A61B 2017/00774* (2013.01); *A61B 2017/22079* (2013.01); *A61B 2017/320004* (2013.01)

(58) Field of Classification Search
  CPC ....... A61B 17/22; A61B 17/50; A61B 17/545; A61B 17/3205; A61B 17/3209; A61B 17/32093; A61B 2017/320008; A61B 2017/320004; A61B 2017/00774; A61B 2017/22079
  See application file for complete search history.

(56) References Cited

U.S. PATENT DOCUMENTS

| | | |
|---|---|---|
| 882,532 A | 3/1908 | McCall |
| 1,882,040 A | 10/1932 | Roehm |
| 1,898,652 A | 2/1933 | Williams |
| 2,228,676 A | 1/1941 | Renga |
| 2,266,931 A | 12/1941 | Wheeler |
| 2,338,339 A | 1/1944 | La Mere et al. |
| 2,608,032 A | 8/1952 | Garver |
| 2,655,146 A | 10/1953 | Force, Jr. |
| 2,701,559 A | 2/1955 | Cooper |
| 2,712,823 A | 7/1955 | Kurtin |

(Continued)

FOREIGN PATENT DOCUMENTS

| | | |
|---|---|---|
| DE | 3421390 | 12/1985 |
| EP | 0258901 | 9/1988 |

(Continued)

*Primary Examiner* — Jocelin Tanner
(74) *Attorney, Agent, or Firm* — Aka Chan LLP

(57) ABSTRACT

A distance between a surface of a treatment head and tip opening of a skin treatment hand piece is adjustable. In an implementation, the distance is adjusted by moving the tip opening relative to the treatment head surface. Different distances may be used to treat different skin types, problems, and conditions. In an implementation, the hand piece includes a fluid delivery and a vacuum or suction mechanism to provide various therapeutic benefits to the skin.

20 Claims, 12 Drawing Sheets

(56) References Cited

U.S. PATENT DOCUMENTS

| | | |
|---|---|---|
| 2,867,214 A | 1/1959 | Wilson |
| 2,881,763 A | 4/1959 | Robbins |
| 2,921,585 A | 1/1960 | Schumann |
| 3,085,573 A | 4/1963 | Meyer et al. |
| 3,236,231 A | 2/1966 | Schneider et al. |
| 3,476,112 A | 11/1969 | Elstein |
| 3,574,239 A | 4/1971 | Sollerud |
| 3,715,838 A | 2/1973 | Young et al. |
| 3,736,921 A | 6/1973 | Kawada |
| 3,818,904 A | 6/1974 | Kawada |
| 3,841,322 A | 10/1974 | Spelio |
| 3,841,323 A | 10/1974 | Stoughton |
| 3,910,284 A * | 10/1975 | Orentreich ........... A61K 8/0208 132/333 |
| 3,964,212 A | 6/1976 | Karden |
| 4,003,373 A | 1/1977 | Spelio |
| 4,182,329 A | 1/1980 | Smit et al. |
| 4,216,233 A | 8/1980 | Stein |
| 4,241,499 A | 12/1980 | Perrone |
| 4,378,804 A | 4/1983 | Cortese, Jr. |
| 4,560,373 A | 12/1985 | Sugino et al. |
| 4,572,187 A | 2/1986 | Schetrumpf |
| 4,646,480 A | 3/1987 | Williams |
| 4,676,749 A | 6/1987 | Mabille |
| 4,706,676 A | 11/1987 | Peck |
| 4,754,756 A | 7/1988 | Shelanski |
| 4,757,814 A | 7/1988 | Wang et al. |
| 4,836,192 A | 6/1989 | Abbate |
| 4,900,316 A | 2/1990 | Yamamoto |
| 4,917,086 A | 4/1990 | Feltovich et al. |
| 4,924,879 A | 5/1990 | O'Brien |
| 4,957,747 A | 9/1990 | Stiefel |
| 5,009,643 A | 4/1991 | Reich et al. |
| 5,012,797 A | 5/1991 | Liang et al. |
| 5,037,431 A | 8/1991 | Summers et al. |
| 5,037,432 A | 8/1991 | Molinari |
| 5,053,024 A * | 10/1991 | Dvoretzky ............. A61F 7/034 604/290 |
| 5,100,407 A | 3/1992 | Conrad et al. |
| 5,100,412 A | 3/1992 | Rosso |
| 5,207,234 A | 5/1993 | Rosso |
| 5,377,701 A | 1/1995 | Fang |
| 5,699,810 A | 12/1997 | Pallikaris |
| 5,800,440 A | 9/1998 | Banuchi |
| 5,810,842 A | 9/1998 | Di Fiore et al. |
| 5,873,881 A | 2/1999 | McEwen et al. |
| 5,954,730 A | 9/1999 | Bernabei |
| 5,961,475 A | 10/1999 | Guitay |
| 5,971,999 A | 10/1999 | Naldoni |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,120,512 A | 9/2000 | Bernabei |
| 6,136,008 A | 10/2000 | Becker et al. |
| 6,139,553 A | 10/2000 | Dotan |
| 6,139,554 A | 10/2000 | Karkar et al. |
| 6,149,634 A | 11/2000 | Bernabei |
| 6,162,232 A | 12/2000 | Shadduck |
| 6,196,982 B1 | 3/2001 | Ball |
| 6,214,009 B1 | 4/2001 | Toriumi et al. |
| 6,241,739 B1 | 6/2001 | Waldron |
| 6,283,978 B1 | 9/2001 | Cheski et al. |
| 6,299,620 B1 | 10/2001 | Shaddock et al. |
| 6,319,211 B1 | 11/2001 | Ito et al. |
| 6,387,103 B2 | 5/2002 | Shadduck |
| 6,423,078 B1 | 7/2002 | Bays et al. |
| 6,500,183 B1 | 12/2002 | Waldron |
| 6,511,486 B2 | 1/2003 | Mercier et al. |
| 6,544,201 B1 | 4/2003 | Guitay |
| 6,629,983 B1 * | 10/2003 | Ignon .................... A61B 17/54 606/131 |
| 6,641,591 B1 | 11/2003 | Shadduck |
| 6,942,649 B2 | 9/2005 | Ignon et al. |
| 7,670,352 B1 | 3/2010 | Starnes |
| 2001/0037118 A1 * | 11/2001 | Shadduck ........... A61B 17/545 606/131 |
| 2002/0016601 A1 | 2/2002 | Shadduck |
| 2002/0107527 A1 | 8/2002 | Burres |
| 2002/0128663 A1 | 9/2002 | Mercier et al. |
| 2002/0133149 A1 | 9/2002 | Bessette |
| 2002/0165564 A1 | 11/2002 | Danitz et al. |
| 2003/0212415 A1 | 11/2003 | Karasiuk |
| 2004/0127914 A1 | 7/2004 | Chung |
| 2004/0138680 A1 * | 7/2004 | Twitchell ............... A61B 17/54 606/131 |
| 2004/0143274 A1 | 7/2004 | Shadduck |
| 2004/0162565 A1 | 8/2004 | Carson et al. |
| 2005/0234477 A1 | 10/2005 | Brown et al. |
| 2007/0088371 A1 | 4/2007 | Karasiuk |
| 2008/0082058 A1 * | 4/2008 | Wallach ................. A61B 17/54 604/293 |
| 2008/0255586 A1 * | 10/2008 | Greenberg ............ A61B 17/54 606/131 |

FOREIGN PATENT DOCUMENTS

| | | |
|---|---|---|
| IT | 1184922 | 10/1987 |
| KR | 10-2004-0093706 A | 11/2004 |
| KR | 10-2006-0031262 A | 4/2006 |
| WO | 9923951 | 5/1999 |
| WO | 00/67692 | 11/2000 |
| WO | 2008052198 A2 | 5/2008 |

* cited by examiner

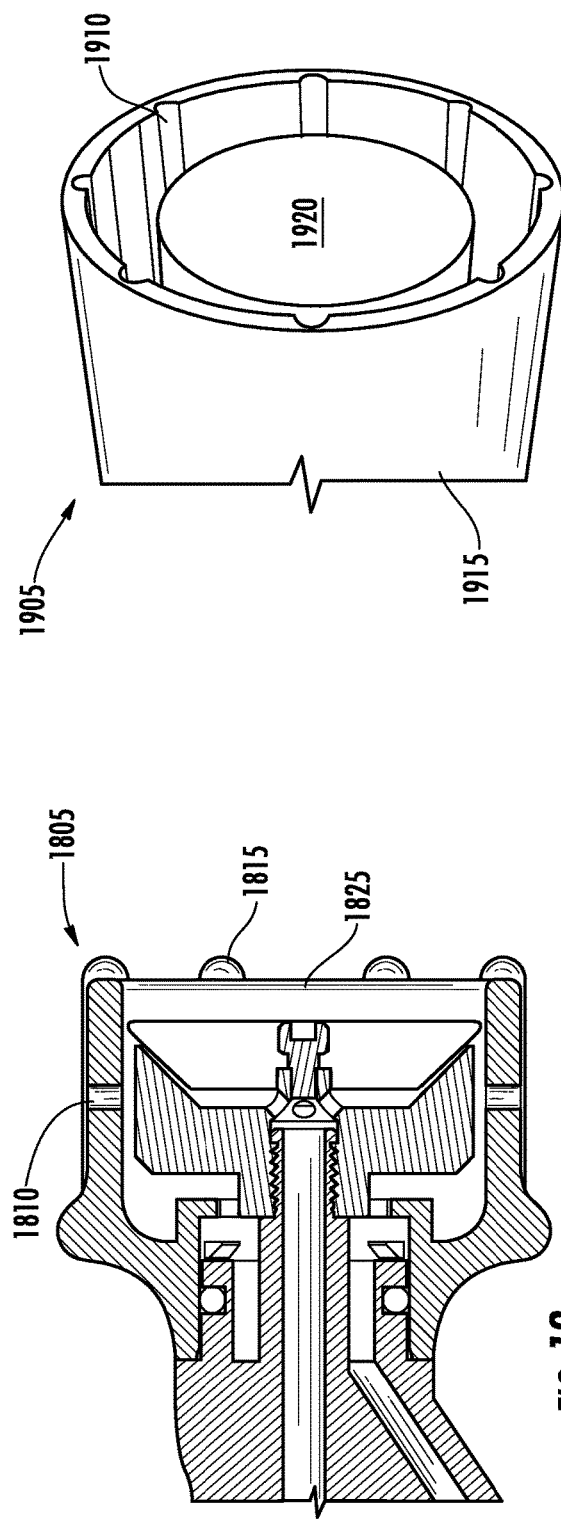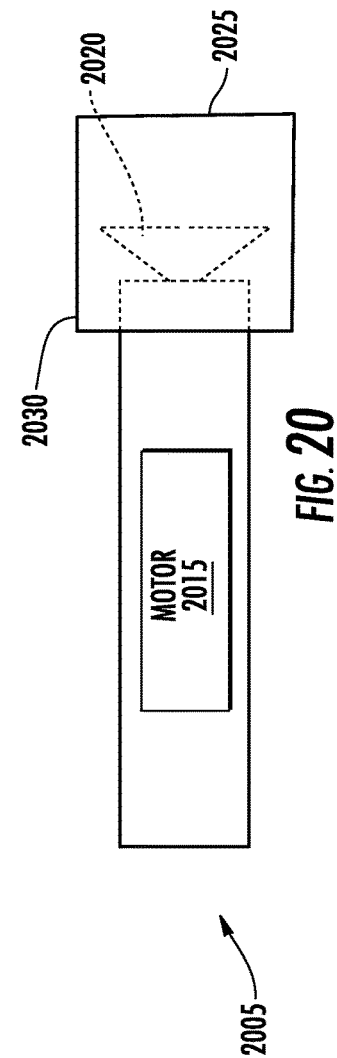

SKIN TREATMENT SYSTEM WITH ADJUSTABLE HEIGHT WAND

CROSS-REFERENCE TO RELATED APPLICATIONS

This patent application is a divisional of U.S. patent application Ser. No. 12/645,210, filed Dec. 22, 2009, issued as U.S. Pat. No. 9,050,133 on Jun. 9, 2015, which is incorporated by reference along with all other references cited in this application.

BACKGROUND OF THE INVENTION

The invention relates to the field of devices to treat human skin and more specifically to a skin treatment system having a hand piece with an adjustable tip.

The skin includes multiple layers of tissue (e.g., hypodermis, dermis, and epidermis) and guards the underlying muscles, bones, ligaments, and internal organs. The skin helps to regulate heat and protects the body against pathogens and water loss. Any open wounds such as cuts, punctures, and scraps should be properly treated so that the tissue does not become infected. The skin also plays a key role in aesthetics and appearance. Smooth and luminous skin is generally desirable as it may be associated with youth, good health, beauty, and fertility.

Treating the skin with certain fluids, solutions, or formulations can be beneficial to the skin tissue. For example, an open wound may be irrigated with solutions such as a saline or antiseptic solution. Certain fluids or solutions can be used to treat cosmetic problems such as cellulite and other blemishes. Such solutions can promote lipid metabolism in skin cells, stimulate blood circulation, nourish and clean the skin, and promote the reduction of cellulite.

Some examples of cosmetic techniques for treating the skin include dermabrasion, microdermabrasion, and massage. Dermabrasion is a surgical procedure that can include removing the epidermis and part of the dermis. Dermabasion can be used to treat scars, superficial skin lesions, and remove tattoos. The procedure is typically performed by a physician using a power tool having a rotating abrasive head or wire brush. The patient may be given sedatives, local anesthetics, and narcotics. There can be bleeding and scabbing after treatment. Recovery after a dermabrasion procedure can be about several weeks. During that time, the skin is fragile. An antibacterial dressing may used to protect the skin as the skin heals.

Microdermabrasion can be an improvement over dermabrasion in that there is typically no significant scabbing or prolonged recovery time. Microdermabrasion is a process for removing dead cells from the outermost layer of the skin (the epidermis) to provide a younger and healthier looking appearance, diminish wrinkles, clean out blocked pores, alleviate certain types of undesirable skin conditions that can develop, and enhance skin tone. Microdermabrasion can help smooth rough skin and acne scars.

Massage is another technique for treating the skin. Massage including a vacuum-based massage can be used to reduce cellulite. Cellulite occurs when fat accumulates in the upper layers of the skin and forms lumps that are visible through the skin. Cellulite can be caused by any number of factors some of which include lifestyle, hormones, heredity, and diet. Massage helps to stimulate the circulatory and lymphatic systems that break down fatty tissue, various pockets of fat, cellulite, and so forth. Massage can be used to target specific areas of the body that are difficult to stimulate with exercise such as the inner knee and upper thigh areas. Massage may also be used to remove stretch marks, such as stretch marks after pregnancy, and restore elasticity to the skin.

The treatment of an open wound on the skin includes the removal of dead tissue (i.e., debridement). The process may include the use of tools such as scalpels, tweezers, and brushes. Failure to properly clean an open wound can lead to infections which in turn can lead to life threatening complications.

Given the particular significance of skin, there is a continuing demand for effective ways to treat the skin. This includes treating skin problems or skin-related conditions (e.g., cellulite, skin blemishes, acne, and scars) and wounds on the skin (i.e., open wounds) such as tears, cuts, punctures, and scrapes. Current skin treatment systems fail to properly integrate fluid delivery mechanisms in their treatment of skin problems, conditions, and ailments.

Therefore, there is a need to provide improved skin treatment systems and techniques.

BRIEF SUMMARY OF THE INVENTION

A distance between a surface of a treatment head and tip opening of a skin treatment hand piece is adjustable. In an implementation, the distance is adjusted by moving the tip opening relative to the treatment head surface. Different distances may be used to treat different skin types, problems, and conditions. In an implementation, the hand piece includes a fluid delivery and a vacuum or suction mechanism to provide various therapeutic benefits to the skin.

The invention described herein relates to a skin treatment system having a hand piece that includes an adjustable-depth tip. In various implementations, the hand piece is used during a microdermabrasion procedure or during a vacuum-based massage procedure. The distance between the surface of the treatment head and tip opening of the hand piece is adjustable. In an implementation, the distance is adjusted by moving the tip opening relative to the treatment head surface. Different distances may be used to treat different skin types, problems, and conditions.

In a specific implementation, the distance between the plastic tip of a hand piece and a surface (e.g., smooth surface or abrasive diamond surface) of the treatment head, is adjustable. The adjustments allow the plastic tip to telescope up and down relative to the treatment head and "click" into one of several different depths. In various implementations, a hand piece with a 15-millimeter diameter treatment head has three levels. A hand piece with a 25-millimeter diameter treatment head has four levels.

One advantage of this feature is the hand piece's ability to pull and fold skin more or less as part of the skin treatment procedure. This action may have a positive impact in targeting conditions such as cellulite and stretch marks. For example, a deeper setting (depth of head relative to tip) may be beneficial in treating a patient who has lost elasticity, suffers from cellulite, or both. The skin is stretched farther and kneaded more as it pulls up into the hand piece.

The more shallow settings (the surface of the head being closer to opening) may be advantageous when treating younger skin, more delicate skin, or sensitive skin. Examples include treating acne and other conditions that can occur on the back or treating stretch marks resulting from weight loss or pregnancy.

Variation of the depth (of head relative to tip) may also contribute positively in treating areas of greater sensitivity, by increasing the skin contact with an abrasive surface of the treatment head without changing the roughness of the abrasive or the vacuum pressure of the device. Reducing patient discomfort offers an improvement over current microdermabrasion hand pieces.

In a specific implementation, a skin treatment hand piece includes a tip. The tip includes a treatment surface and a tip opening. A distance between the tip opening and the treatment surface is adjustable. The treatment surface may be connected to an end of a tubular passageway. The tip opening may be provided by an adjusting collar rotatable about the tubular passageway throughout a range of positions thereby adjusting the distance. In an implementation, at each position the treatment surface does not extend past the tip opening.

The hand piece may further include an indexing assembly for releasably retaining the adjusting collar in a selected angular position. The selected angular position can be overcome by a user applying torque to the adjusting collar. The indexing assembly may further include a ball detent, where a ball of the ball detent is urged via a spring into a set of detents formed on the tubular passageway.

In a specific implementation, a device includes a treatment surface connected to a first structure and a second structure connected to the first structure and including a first end having a tip opening. The treatment surface can be positioned within the second structure and is exposed by the tip opening. The second structure is movable relative to the first structure, thereby allowing altering of a position of the treatment surface relative to the tip opening.

The second structure may be removably connected to the first structure. The second structure may be rotatable about an axis of the first structure. The first structure may include a tubular passageway, and a flow path of a fluid including a liquid may be from a distal end of the tubular passageway to the treatment surface, away from a center of the treatment surface, and into an annular space surrounding at least a portion of the tubular passageway. An O-ring may be between the first and second structure. In a specific implementation, the treatment surface is abrasive. In another implementation, the treatment surface includes no abrasive particles.

In a specific implementation, there is a third structure to which the second structure is removably connected. The third structure can be rotated about an axis of the first structure. There is a first O-ring between the first and second structures. There is a second O-ring between the second and third structures.

The device may further include a suction port connected to the first structure. A first distance from the suction port to the tip opening may be greater than a second distance from the treatment surface to the tip opening. A third distance between the suction port and treatment surface may remain fixed as the position of the treatment surface relative to the tip opening is altered.

In a specific implementation, a method of treating skin includes changing a distance between an opening of a treatment tip to a treatment surface, applying the treatment tip to a skin surface, providing suction outside a periphery of the treatment surface through the opening, and drawing a portion of the skin surface through the opening using the suction. The portion of the skin surface drawn is proportional to the distance. The distance may be changeable within a range from about 4 millimeters to about 15 millimeters.

In a specific implementation, the opening of the treatment tip is provided by a sleeve having a set of interlocking sleeve pieces and the changing a distance between an opening of a treatment tip to a treatment surface includes removing a first interlocking sleeve piece. The method may further include providing a fluid to the portion of the skin surface using the suction, where the fluid does not exit the opening.

In another implementation, the treatment surface is provided by a first treatment head having a first thickness and the changing a distance between an opening of a treatment tip to a treatment surface includes replacing the first treatment head with a second treatment head having a second thickness, different from the first thickness.

In a specific implementation, the skin surface includes a wart caused by a human papillomavirus (HPV) infection, and the method further includes moving the treatment tip over the wart and, using abrasive particles of the treatment surface, removing a layer of dead skin on the wart, and providing a treatment liquid via the treatment tip to tissue below the layer of dead skin. In another implementation, the skin surface includes hyperkeratotic tissue, and the method further includes moving the treatment tip over the hyperkeratotic tissue and, using abrasive particles of the treatment surface, removing at least a layer of the hyperkeratotic tissue, and providing a treatment liquid via the treatment tip to tissue below the layer of hyperkeratotic tissue. The hyperkeratotic tissue may include a callus.

In a specific implementation, an adjustable-depth skin treatment kit includes a container, including a set of treatment head spacers where at least one spacer is to be placed behind a treatment head. The kit further includes a microdermabrasion hand piece, connected to or capable of being connected to the treatment head. The hand piece includes a tip opening. When a first spacer is placed behind the treatment head, a first depth is from the tip opening to the treatment head, and when a second spacer is placed behind the treatment head, a second depth, different from the first depth, is from the tip opening to the treatment head.

The first spacer may have a first color indicating a thickness of the first spacer, and the second spacer may have a second color, different from the first color, indicating a thickness of the second spacer. A thickness of the first spacer may be different from a thickness of the second spacer. A diameter of the at least one spacer may be less than a diameter of the tip opening.

In a specific implementation, a method includes positioning a treatment tip over an open wound, providing a suction outside a periphery of an abrading surface through at least one opening of the treatment tip, drawing a portion of the open wound into contact with the abrading surface using the suction, providing a treatment liquid via the treatment tip to the open wound, moving the treatment tip over the open wound and debriding the portion of the open wound in contact with the abrading surface, and drawing a liquid away from the abrading surface through the at least one opening of the treatment tip. A flow path for the treatment liquid is from a distal end of a tubular passageway, outward at the treatment tip, into the at least one opening of the treatment tip, and into an annular space surrounding at least a portion of the tubular passageway.

The treatment liquid may include at least one of an antiseptic or antibiotic solution. The liquid may include at least a portion of the treatment liquid and infected tissue particles.

Other objects, features, and advantages of the present invention will become apparent upon consideration of the following detailed description and the accompanying draw-

BRIEF DESCRIPTION OF THE DRAWINGS

FIG. 18 shows a side view of a hand piece having a breather hole and massaging nodes.

FIG. 19 shows a perspective view of a hand piece having fluid delivery channels.

FIG. 20 shows a side view of a hand piece having a motor to provide a reciprocating action.

DETAILED DESCRIPTION OF THE INVENTION

Figure 1:
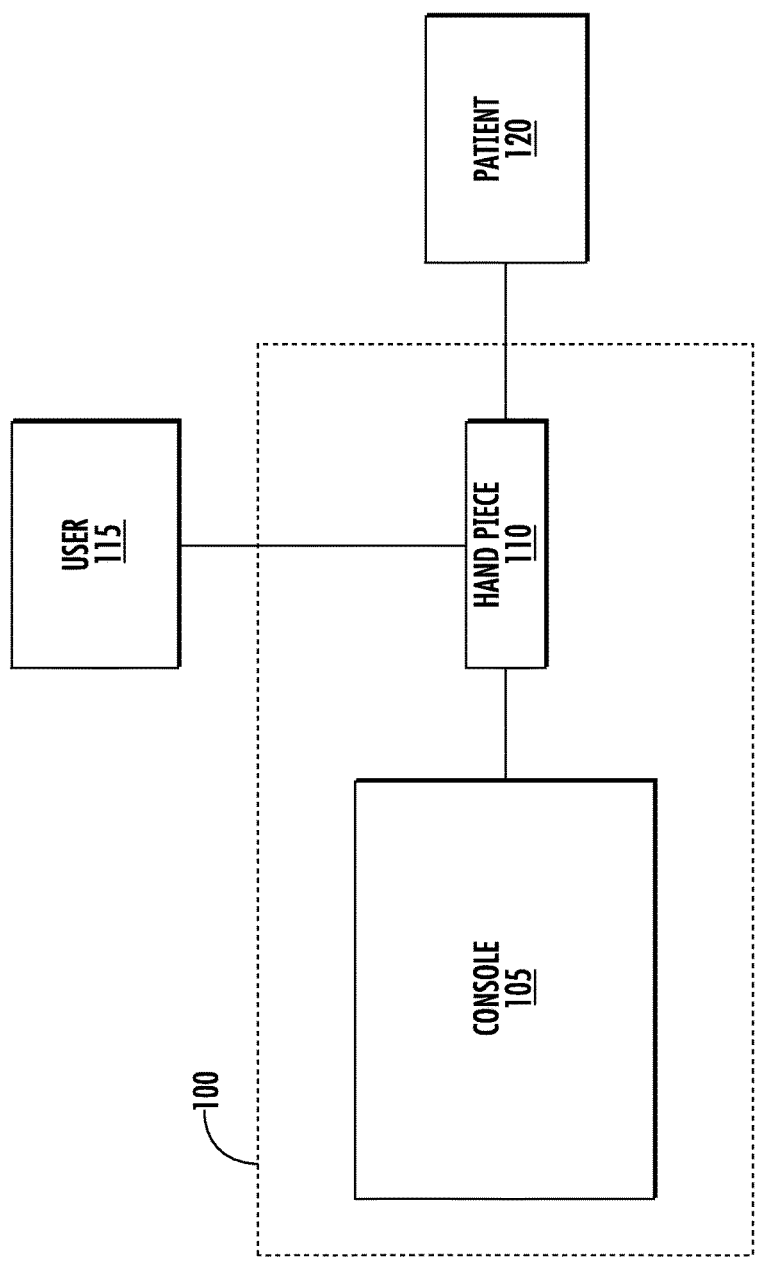
FIG. 1 shows block diagram of a skin treatment system according to the present invention.

FIG. 1 is a simplified block diagram of a skin treatment system 100. The system has a console 105 which is connected to a hand piece 110. During a treatment session, a user 115 holds the hand piece and runs the hand piece over a patient's 120 skin. The user may be a doctor, physician, surgeon, dermatologist, nurse, technician, operator, or aesthetician.

A specific implementation of this invention is a hand piece having an abrasive treatment head or surface for performing microdermabrasion or dermabrasion. The hand piece can include any type of treatment surface for treating the skin. For example, the hand piece can include an abrasive treatment surface to exfoliate the skin. As another example, the hand piece can include a smooth or nonabrasive treatment surface to shine or polish the skin. During the treatment, a pressurized fluid delivery feature of the system can provide treatment fluids to the skin. Such fluids can be infused into the skin to provide therapeutic benefits. After treatment, the patient leaves with a more youthful and healthful appearance.

This skin treatment system can be used to treat many different types of skin problems, conditions, or ailments. For example, a specific implementation of this invention is the removal of dead skin on the surface of skin infected with human papilloma virus (HPV). The infection may be on internal or external skin, such as on the foot or in the mucous membranes of a patient such as oral mucosa or cervix. Features of the invention, such as the abrasive treatment head, can remove or get rid of the dead skin that prevents the therapeutic solution from reaching the area of interest. Generally, salicylic acid does not penetrate through the dead skin of a wart. Features of the invention can address that.

This skin treatment system may also be used to treat various types of hyperkeratotic skin ailments that require removal of dead skin on the feet or other large body locations. Some examples of hyperkeratotic skin ailments include calluses, corns, warts, chronic eczema, lichen planus, actinic keratoses, seborrheic keratoses, and the like.

Another specific implementation of this invention is for the treatment of open wounds. For example, an abrasive treatment head can be used with this hand piece for debridement of open wounds. That is, a surgeon can use this hand piece to treat a patient having an open wound that is contaminated, dirty, or infected. The abrasive treatment head of the hand piece can be used to provide mechanical abrasion to debride the tissue and remove necrotic or dead skin in the wound. Fluids such as a saline, antibiotic, or antiseptic solution can be provided by the fluid delivery system to treat the wound. The combination of a pressurized fluid delivery system and mechanical abrasion is an advantage over current system which merely offer pressurized saline delivery in the operating room.

Figure 2:
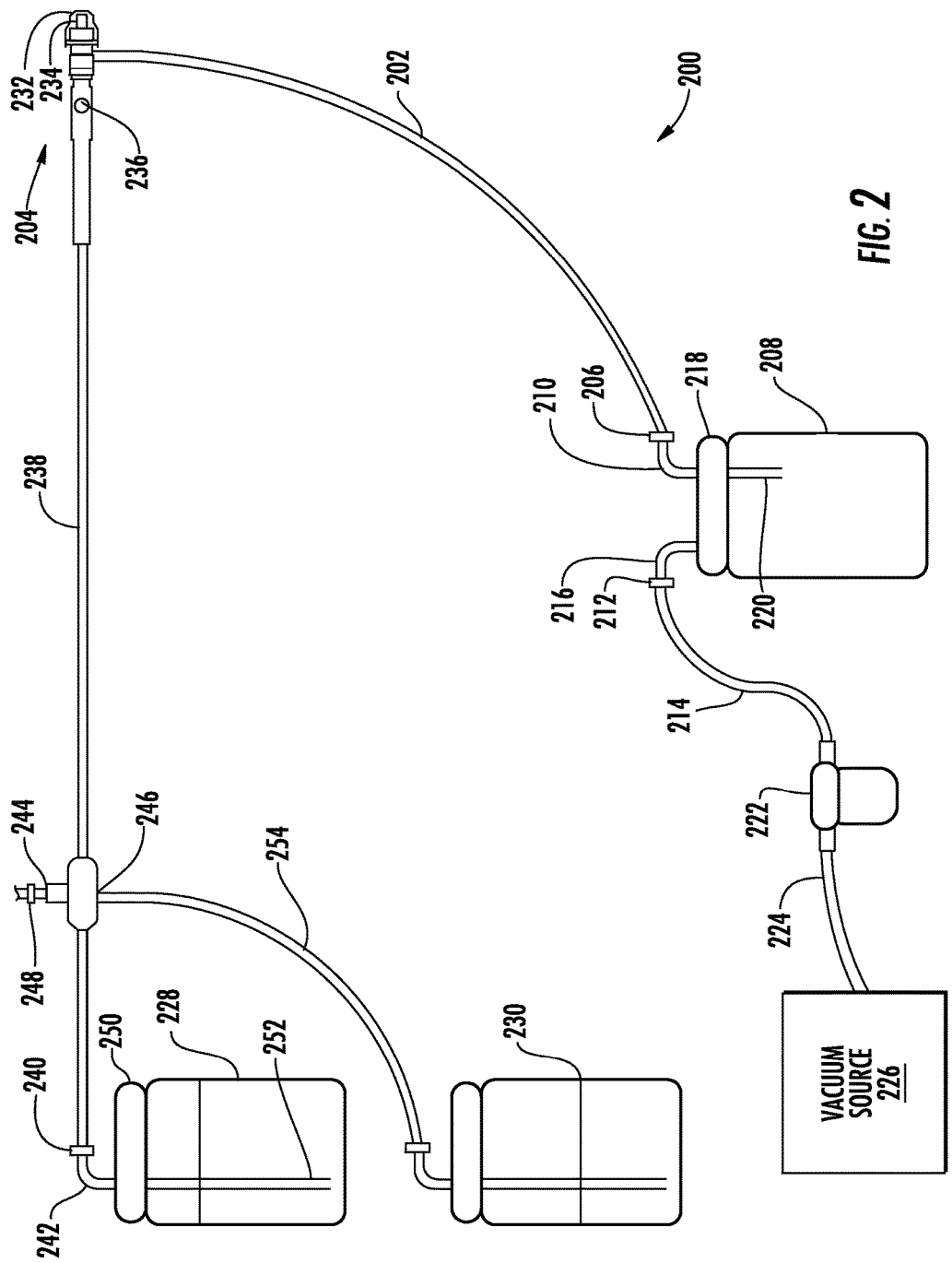
FIG. 2 shows an illustration of a skin system.

FIG. 2 shows an overview of the flow of a skin treatment system 200. A vacuum line 202 is connected to a wand or hand piece 204. Vacuum line 202 connects to an input 206 to a collection reservoir 208 via an elbow 210, for example. An output 212 connects with a second vacuum line 214 via an elbow 216, for example. A manifold cover 218 seals the input (206, 210) and output (212, 216) connections with collection reservoir 208 which is typically a jar made of glass or plastic, for example. An extension tube 220 connects with inputs 210 and 206 and extends into the collection reservoir. The collection reservoir holds the waste materials (e.g., abraded skin particles, infected skin particles, and, optionally, fluids) from the skin treatment process.

Optionally, a filter 222 may be provided between second vacuum line 214 and a third vacuum line 224 which connects to a vacuum source 226. Filter 222 ensures that no fluid, skin particles, abrasive particles, or other materials collected by collection reservoir 208 are transported to vacuum source 226.

Any type of filter may be used. For example, in a specific embodiment, filter 222 is an in-line condensation or hydrophobic filter, such as a water condenser produced by Wilkerson Labs and available as part number F0001-000 from Nor-Cal Controls, Inc. of San Jose, Calif.

Vacuum source 226 may be any type of vacuum source such as a vacuum pump, an ejector (e.g., single-stage ejector and multi-stage ejector), or a vacuum blower. In an implementation, the vacuum source creates negative pressure compared to the pressure at the hand piece tip, so that there is suction at the tip (i.e., there is a pressure difference between the pressure at the vacuum source and tip). Because of this suction or negative pressure, air, fluid, particles, and other matter at the tip are drawn to the vacuum source (through the collection reservoir). Further, in an implementation, the negative pressure also draws fluid out of a first fluid reservoir 228, a second fluid reservoir 230, or both to the tip, where is it pulled back into the collection reservoir. The suction is a fluid path that can conduct any fluid, including liquids, gases, or both.

An example of vacuum sources includes the ProPeel, MDPeel, iPeel, or SilkPeel microdermabrasion systems available from Envy Medical, Inc., Westlake Village, Calif. Vacuum source 226 may generate a vacuum pressure from about 2 pounds per square inch (psi) to about 14 pounds per square inch. For example, the vacuum pressure may be about 3, 4, 5, 6, 7, 8, 9, 10, 11, 12, 13, or more than 14 pounds per square inch. In some embodiments, the vacuum pressure may be less than 2 pounds per square inch.

Vacuum source 226 may include a vacuum pressure adjustment control so that a user can vary the vacuum pressure. In a specific embodiment, the vacuum pressure adjustment control is a knob that can be rotated to change the vacuum pressure. In other embodiments, the vacuum pressure adjustment control is one or more push buttons, a slider bar, or other. A vacuum pressure gauge may indicate the current vacuum pressure. In a specific embodiment, the vacuum pressure gauge is a digital gauge. In another embodiment, the vacuum pressure gauge is a dial gauge.

In a specific embodiment, vacuum source 226 includes a fluid flow adjustment control so that a user can vary the fluid flow settings. The fluid flow may range from about 0 milliliters per minute to about 140 milliliters per minute. For example, the fluid flow may be about 10, 20, 30, 40, 50, 60, 70, 80, 90, 100, 110, 120, 130 milliliters, or more than 140 milliliters per minute. In a specific embodiment, the fluid adjustment control is a knob that can be rotated to change the fluid flow. In other embodiments, the vacuum pressure adjustment control is one or more push buttons, a slider bar, or other. A fluid flow gauge may indicate the current flow rate. In a specific embodiment, the fluid flow gauge is a digital gauge. In another embodiment, the fluid flow gauge is a dial gauge.

Typically, the fluid is not pressurized to such a degree that the fluid will puncture or cut the skin. The fluid may be pressurized to a pressure that may range from about −1 pound per square inch to about 20-12 pounds per square inch. For example, the fluid may be pressurized to a pressure of −2, −3, −4, −5, −6, −7, −8, −9, −10, −11, −12, 13, 14, 15, 16, 17, 18, 19, or 19.9 pounds per square inch. Depending upon the application, the fluid may be pressurized to a pressure less than −1 pound per square inch or greater than −20 pounds per square inch.

In a specific implementation, the suction provided by the vacuum source is solely responsible for drawing fluid from the fluid reservoir to the patient's skin, back into the hand piece, and into the collection reservoir. In this specific implementation, there is no pump to pump fluid from the fluid reservoir to the hand piece. There is no pump at the fluid reservoir. In another implementation, there is a pump to pump fluid from the fluid reservoir to the hand piece. The pump may pressurize the fluid in the fluid reservoir.

Wand 204 includes a tip or treatment head holder 232 which holds a treatment head or tip piece 234. A first fluid delivery line 238 extends from wand 204 and connects to an output 240 of first fluid reservoir 228 via an elbow 242, for example.

A breather line 244 may be connected in-line via a joint 246, for example, or other interconnection, and includes an adjustable valve 248 or other means for varying an amount of air that is allowed into first fluid delivery line 238. This feature allows, for example, the amount of vacuum pressure to be adjusted for a given fluid and allows fluids having different viscosities to be applied at the same vacuum pressure level, since different viscosities will require varying amounts of air to be introduced into breather line 244 to produce a constant vacuum pressure level.

Alternatively, a breather line or input with adjustment valve may be located on elbow 242 or directly on a manifold cover 250. Still further, a valve or other flow control mechanism 236 may be provided on wand 204 or in first fluid delivery line 238 to control the amount of fluid passing through the line. This feature can be provided alternatively, or in addition to breather line 248 discussed above.

The flow control mechanism or valve allows, for example, the user to turn off the flow of fluid to the wand so that the user can clean or replace the tip if it becomes clogged. The fluid flow control mechanism may be located on the wand as shown in FIG. 2 or anywhere along the fluid flow path such as on first fluid delivery line 238. Generally, however, the fluid flow control valve will be located on the wand or near the wand so that the user can quickly turn off the flow of fluid.

An input may be provided in manifold cover 250 which may be open to the atmosphere to prevent vacuum buildup in first fluid reservoir 228. Manifold cover 250 seals output (240, 242) connections with first fluid reservoir 228 which is typically a jar made of glass or plastic, for example, and contains lotions, vitamins, other skin treatment fluids, or combinations of these to be applied to the skin by wand 204. An extension tube 252 connects with output 240, 242 and extends into the first fluid reservoir to near the bottom of the first fluid reservoir to ensure that most all of the contents of the fluid reservoir are capable of being delivered through the system.

In a specific embodiment, second fluid reservoir 230 is also included. A second fluid delivery line 254 connects the second fluid reservoir to joint 246. Joint 246 may further include a valve to block or to permit the flow of fluid from the second fluid reservoir into first fluid delivery line 238.

The first fluid reservoir may include contents that are the same or different from the first fluid reservoir. For example, the first fluid reservoir may include topical anesthetics and the second fluid reservoir may include disinfectants. In various implementations, there are any numbers of fluid reservoirs. For example, an implementation may have more than two fluid reservoirs, such as three, four, five, six, seven, or more than seven fluid reservoirs.

Having more than one fluid reservoir allows, for example, different types of fluids to be used to treat different types of skin conditions that the patient may have without requiring the user to constantly remove the existing fluid reservoir and replace it with a new fluid reservoir that contains the appropriate fluid. For example, a patient with oily skin may require a different treatment regime than a patient with dry skin. The patient with the oily skin may thus be treated with fluid from the first fluid reservoir in which the fluid does not contain any oil-based products because such oil-based products may worsen the patient's skin condition. The patient with the dry skin may instead be treated with fluid from the second reservoir in which the fluid may include oil-based products to help moisturize the skin.

Abrasive particles, such as corundum crystals, sodium bicarbonate particles or other abrasive particles, including those discussed in U.S. Pat. No. 5,971,999 (which is incorporated by reference), for example may be included in the fluid reservoirs for delivery through the system to perform a microdermabrading function. Microdermabrasion is typically accomplished via a bristled tip, abrasive tip, or both. A smooth tip may be used if the patient desires to be treated with fluids and with little or no abrasion, such as during vacuum-massage or vacuum-based cellulite massage. The tips may be used together with any of the fluids mentioned above, with some other fluid carrier medium, such as those described in U.S. Pat. No. 5,971,999, for example, or both.

The fluid reservoirs may contain solution or a suspension for purposes other than abrasion or pure abrasiveness. The compositions used in the present invention can include a wide and diverse range of components. The *International Cosmetic Ingredient Dictionary and Handbook*, 12$^{th}$ edition, 2008, which is incorporated by reference, describes an extensive variety of cosmetic and pharmaceutical ingredients commonly used in the skin care industry, which are suitable for use in the compositions of the present invention.

General examples, types or categories, or both, of compounds that may be employed include: bleaching formulations (e.g., 2 percent to 4 percent hydroquinone, 2 percent kojic acid, 1 percent vitamin K, and 1 percent hydrocortisone in an aqueous base); acne treatment formulations (e.g., salicylic acid, alcohol base buffered by witch hazel, etc.); fine lines/wrinkle treatment formulations (e.g., hyaluronic acid in an aqueous base); hydrating formulations (e.g., calendula, vitamins A, D, E, or other vitamins, or combinations of these in a mineral oil base); antioxidant formulations; free radical scavengers (e.g., vitamins A, E, K, or other vitamins, or combinations of these in a mineral oil base); pH adjusters; sunscreen agents; tanning agents and accelerators; nonsteroidal anti-inflammatory actives (NSAIDS); antimicrobial and antifungal agents; moisturizers; lightening agents; humectants; numbing agents; retinol (e.g., 0.2 percent to about 0.6 percent concentration); saline; and water, or combinations of these.

The solution or suspension may contain extracts such as those from plants, vegetables, trees, herbs, flowers, nuts, fruits, animals, or other organisms, or combinations of these. Such extracts may be used to help condition the skin, provide a relaxing aroma, or both.

The solution or suspension may also contain viscosity increasing or decreasing agents, colorants, or combinations of these. In a specific implementation of the invention, the viscosity of the fluids used is about 1 centipoise (e.g., about 0.5 to 1.5 centipoise). However, in other implementations, the viscosity may range from 0.1 centipoise to 100 centipoises. The viscosity may be, for example, 0.2, 0.3, 0.4, 0.5, 0.6, 0.7, 0.8, 0.9, 1, 1.1, 1.2, 1.3, 1.4, 1.5, 1.6, 10, 20, 30, 40, 50, 60, 70, 80, 90, or more than 100 centipoises. In other applications the viscosity may be less than 0.1 centipoise.

In a specific implementation, the fluids, abrasive particles, or both for the fluid reservoirs may be packaged as a concentrated solution, powder, solids, or combinations of these to be mixed, diluted, or both by the microdermabrasion system, user, or both.

Other examples of product categories that may be employed alone or in combination with other compounds include, antibiotics, antiseptics, disinfectants, astringents, cleansers, pore decongestants, balms, botanicals, collagen stimulators, herbs, microemulsifiers, oxygen delivery vehicles, proteins, serums, skin firming agents, toners, topical anesthetics, emulsions, ointments, gels, tyrosinase inhibitors, anti-cellulite oils, and other related product categories. Anti-cellulite oils may include one or more of the following oils hazelnut, jojoba, cinnamon-leaf, juniper, rosemary, cypress, orange, grapefruit, cedarwood, lemon, or lime.

Individually named products that may be used (with associated benefit indicated parenthetically) include: Aloe Vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); hydroquinones (bleaching); lactic acids (peel); magnesium ascorbic phosphate (free radical scavenger, collagen stimulator, bleaching); niacin (vascular dilation); phospholipids (moisturization); potassium (toning, psoriasis), and salicylic acids (acne); and related products.

Of course, any combination of such elements may be provided—even in connection with abrasive particles.

Any of the products listed may be used with the microdermabrasion hand piece of the invention. For example, fluids which help to clarify the skin (e.g., clarifying infusions) may be used. Fluids which help to hydrate the skin (e.g., hydrating infusions) may be used.

As another example, coenzyme Q-10, glycolic acids, or vitamin E, to name a few examples, may be conducted through an opening of the treatment head to the skin of a patient. The opening may extend to a position closer to patient's skin through a cylindrical column, nipple, or other structure to achieve a similar purpose.

Note, however, the present system may be used by eliminating the fluid reservoirs altogether, where microdermabrasion or vacuum massage is performed in a "dry state" and first fluid delivery line 238 is simply left open to atmosphere, with or without a filter or valve, or both, for adjusting the amount or flow rate of air that is allowed into the first fluid delivery line. Similarly, dry or externally lubricated vacuum massage of tissue may be accomplished by tip 234 having a smooth surface.

A feature of the invention is that the system delivers fluids directly to the patient's skin while simultaneously exfoliating the skin, removing dead or necrotic skin in an open wound, or removing dead skin to treat the underlying skin (e.g., treating hyperkeratotic tissue such as a callus). In an embodiment, the system uses a variety of specially formulated solutions to provide, for example, treatment for hyperpigmentation, dehydration, acne, and photodamage. In another embodiment, specially formulated solutions are used during debridement of open wounds. These solutions can include an antibiotic, an antiseptic, or both.

Patients receive the most benefit when fluids are used to treat their skin-specific conditions that have specifically been tested and approved for use with the system. These fluids also provide a consistent level of quality. Furthermore, these fluids are tested in the system to ensure that they do not clog the system.

Unapproved fluids may not have been tested and have an uncertain quality. They may fail certain quality standards. Unapproved fluids, for example, may not contain active ingredients, may contain an insufficient quantity of active ingredients, may contain entirely incorrect ingredients, may contain improper proportions of ingredients, or may even contain hazardous ingredients. A patient who receives unapproved fluids as part of their skin treatment may suffer dangerous consequences to their health, such as unexpected side effects, rashes, allergic reactions, a worsening of their skin condition, or other problem. Unapproved fluids, because they have not been tested in the system, may also clog the system.

Figure 3:
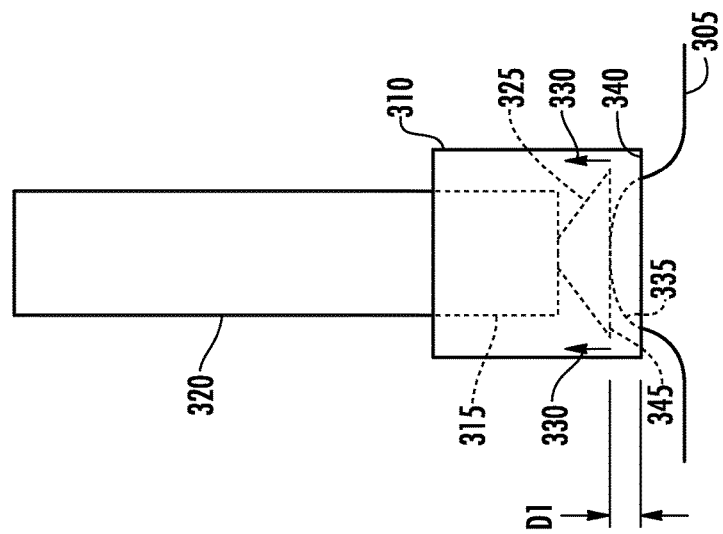
FIG. 3 shows a block diagram of a skin treatment hand piece having an adjustable tip adjusted to a first depth.

FIG. 3 shows a more detailed block diagram of a specific implementation of the hand piece shown in FIG. 1 being applied to skin 305 of the patient. The hand piece includes an adjustable tip 310 that fits over or is attached to a distal end 315 of a handle 320. A treatment head or tip piece 325 is attached to the distal end and may be part of the tip. A suction or vacuum as shown by arrows 330 pulls a targeted portion 335 of skin through an opening 340 of the tip so that the treatment head can treat or abrade the targeted skin.

A depth, height, or distance D1 is measured between tip opening 340 and a surface 345 of the treatment head. In FIG. 3, depth D1 has been adjusted to a first depth. A user can adjust depth D1 and thus vary the distance that the skin is pulled into the tip opening.

Figure 4:
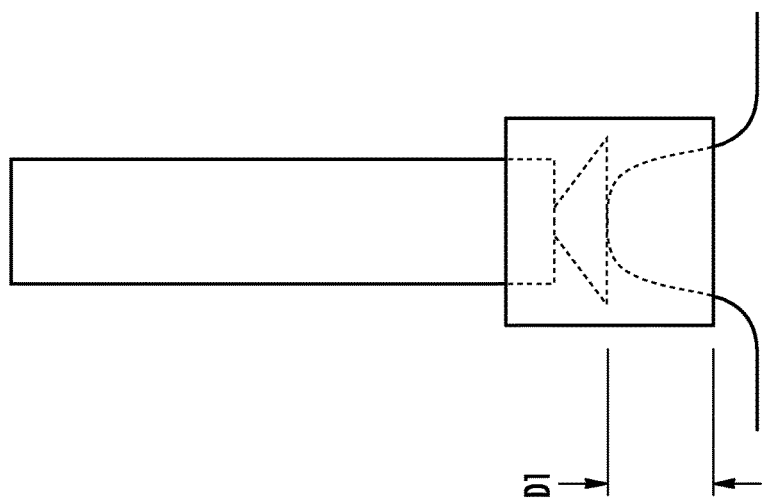
FIG. 4 shows a block diagram of the hand piece adjusted to a second depth.

FIG. 4 shows a block diagram of the hand piece where the user has adjusted depth D1 to a second depth. As shown in the examples of FIGS. 3-4, the second depth is greater than the first depth. This allows a greater amount of skin to be lifted, stretched, pulled, or folded as compared to the position of the adjustable tip shown in FIG. 3. This adjustment feature can be used to target specific conditions such as cellulite and stretch marks. For example, a deeper or high setting, such as shown in FIG. 4, can be beneficial in treating a patient who has lost elasticity in their skin, is being treated specifically for cellulite, or both. The skin is stretched farther and kneaded more as it is pulled up into the hand piece as compared to the shallow setting shown in FIG. 3. The high setting can be used to provide deep lymphatic massage.

The shallow setting (FIG. 3) may be advantageous when treating younger patients or patients whose skin is more delicate and sensitive. This hand piece can be used to treat acne, other skin conditions that occur on the patient's back, stretch marks such as resulting from weight loss or pregnancy, or combinations of these.

The opening of the adjustable tip can telescope up and down relative to the treatment head. In a specific implementation, a treatment surface is connected to a first structure, such as an end of a handle. A second structure is connected to the first structure and includes a tip opening. The treatment surface can be positioned within the second structure and is exposed by the tip opening. This allows the treatment surface to contact the skin that is lifted into the tip opening. The second structure is movable relative to the first structure. This allows altering of a position of the treatment surface relative to the tip opening.

Any mechanism may be used to allow the user to adjust the distance between the tip opening and the treatment head (or treatment surface). For example, the second structure may be removably connected to the first structure. This allows the second structure to be swapped or replaced with a third structure having different dimensions (e.g., lengths or heights) than the second structure so that the position of the treatment surface relative to the tip opening can be altered.

In a specific implementation, depth D1 is adjusted by rotating adjustable tip 310 relative to the treatment head. This rotation produces an axial displacement of the adjustable tip relative to the treatment head. The adjustable tip translates along the handle and rotates about the handle.

In this specific implementation, depth D1 is increased by rotating the adjustable tip in a clockwise direction. Depth D1 is decreased by rotating the adjustable tip in an opposite or a counterclockwise direction as seen from a proximal end of the hand piece and looking towards the distal end. However, it should be appreciated that these directions can be swapped, i.e., rotate in clockwise direction to decrease depth D1; rotate in counterclockwise direction to increase depth D1.

In another implementation, depth D1 is adjusted by pulling or pushing the adjustable tip relative to the treatment head. The adjustable tip translates along the handle, but does not rotate about the handle. For example, depth D1 can be increased by pulling the adjustable tip away from the treatment head. Depth D1 can be decreased by pushing the adjustable tip towards the treatment head. The adjustable tip can slide along a linear track, guide, or rail.

Depth D1 may be adjusted by swapping tips, tip parts, or both. For example, a first tip may provide a first depth between an opening of the first tip and a treatment head. A second tip may provide a second depth, different from the first depth, between an opening of the second tip and the treatment head. The user can remove the first tip from the hand piece and attach the second tip to the hand piece. The tips can be attached using threads (i.e., tip screws onto hand piece). The tips can be attached frictionally to the hand piece such as using a press or interference fit. The tips can be attached using a snap-fit, set screws, bolts, nuts, screws, dowels, or any other connection type or combination of connection types.

In another specific implementation, the tip and handle are fixedly connected. That is, the tip and handle are stationary and do not move. In this specific implementation, the distance between the treatment head and the tip opening is adjusted by moving the treatment head relative to the tip opening. For example, the treatment head may be attached to a sliding carrier, platform, or sled. A slide or switch on the handle allows the user to slide the carrier and thus the treatment head forwards and backwards with respect to the tip opening. The treatment head can be locked into any number of positions. As another example, the treatment head is connected to a threaded rod. Turning the rod with respect to the handle in one direction moves the treatment head forwards. Turning the rod in an opposite direction retracts the treatment head. The treatment head may be connected to a rod that can be pushed and pulled with respect to the handle. The rod may include teeth which engage with a pawl of a ratchet mechanism so that the treatment head can be locked into position.

Depth D1 may be adjusted from about 1 millimeter to about 20 millimeters. This includes, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 19.9 millimeters. Depth D1 may be adjusted to a depth less than 1 millimeter or greater than 20 millimeters. In various implementations, depth D1 is adjustable within a range from about 5 millimeters to about 15 millimeters. Depth D1 is adjustable within a range from about 4 millimeters to about 7 millimeters.

Generally, the treatment head does not extend past the tip opening. This allows the patient's skin to be pulled into the tip opening. In a specific implementation, there is a stop member or other feature that prevents the user from extending the treatment head past the tip opening. However, in another implementation, the treatment head or a portion of the treatment head can extend past the tip opening.

Figure 5:
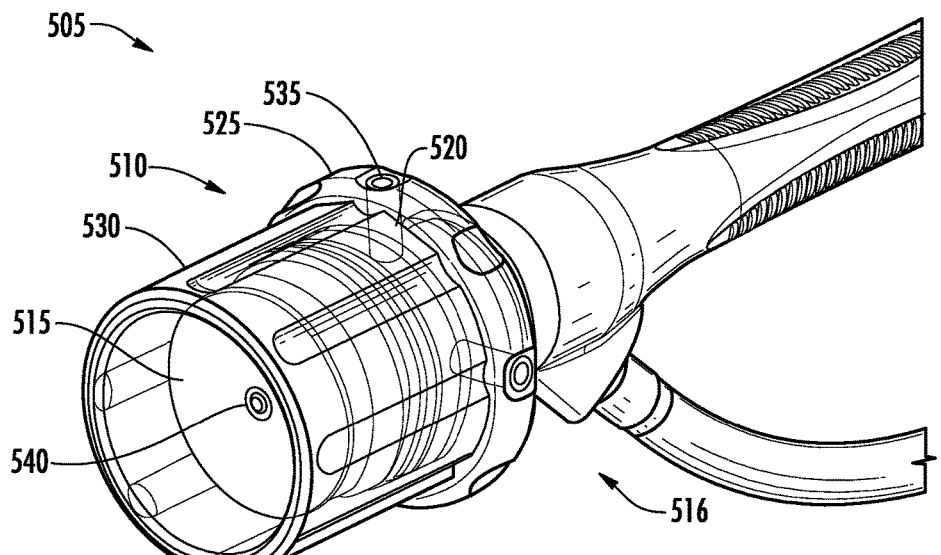
FIG. 5 shows a perspective view of a first embodiment of a skin treatment hand piece with an adjustable tip.

FIG. 5 shows a perspective view of a first embodiment of a hand piece 505 having an adjustable tip 510 and a treatment head 515 at a distal end 516 of the hand piece. The adjustable tip includes an adjusting collar 520 having a flange 525 and a sleeve (e.g., cylinder, extension, tube, or attachment) 530 which is attached to the collar and butted up against a side of the flange. A set of pegs 535 are arranged about the flange and pass through a side edge or side surface of the flange.

A screw 540 is used to fasten the treatment head to the distal end of the hand piece. Typically, the screw is recessed below the surface of the treatment head so that the head of the screw does not scratch the patient's skin. The screw drive type can be a hex socket head (as shown in the figure), slotted, Phillips, Pozidriv, square, Robertson, hex, torx, tri-wing, torq-set, spanner head, triple square, polydrive, one-way, spline drive, double hex, Bristol, and so forth.

The screw allows the user to replace the treatment head. That is, the treatment heads can be interchangeable. For example, the user can unscrew the screw, remove a treatment head having an abrasive treatment surface, and place a treatment head having a smooth treatment surface onto the hand piece. Thus, this feature allows the user to select the appropriate level of abrasiveness for the patient's skin.

Any mechanism may be used to fasten or attach the treatment head to the hand piece. For example, a treatment head may instead or additionally be attached using an interference or press fit, snap-fit, threads, or any other kind of locking mechanism (e.g., insert treatment head, and then twist or screw to lock).

In a specific implementation, the treatment head is designed to be reusable. A treatment head can be removed, cleaned, and then placed back onto the hand piece to be reused. For example, the treatment head may be designed to be autoclavable (i.e., sterilized by being subjected to high-pressure steam at 121 degrees Celsius or more).

In another implementation, the treatment head is designed to be disposable, such as after a onetime use. Some disposable treatment heads are further discussed in U.S. patent application Ser. No. 12/040,867, filed Feb. 29, 2008 which is incorporated by reference along with all other references cited in this application.

Generally, the collar is frictionally fit over the distal end of the handle. One or more gaskets such as O-rings or other sealing members may be placed between the collar and the distal end of the handle. This helps to create a seal so that fluid does not leak out.

The flange may include one or more notches, grooves, or recesses distributed about or around a circumference of the flange. Similarly, the sleeve may include one or more notches distributed about or around a circumference of the sleeve. The notches help to ensure that the user's fingers do not slip while adjusting the adjustable tip. In an implementation, the user adjusts the tip by rotating the collar relative to the treatment head. The user can grasp the flange, sleeve, or both and turn or twist the collar in a first direction to extend the distance between the tip opening and the treatment surface. The user can turn the collar in a second direction, opposite the first direction, to reduce the distance between the tip opening and the treatment surface.

The surface of the flange, sleeve, or both may instead or additionally be textured to prevent slipping. The texturing may include raised surfaces or ridges, a roughened surface, knurls, cuts, grooves, and the like. Any process may be used to create a textured surface such as machining, knurling, chemical etching, or grit blasting.

The sleeve may be made of a transparent, semitransparent, translucent, or semitranslucent material. This allows the user to view the patient's skin during the microdermabrasion treatment. The sleeve may instead be made of an opaque material. The sleeve may be made of plastic such as nylon, thermoplastics, polyethylene, polycarbonate, acrylonitrile butadiene styrene (ABS), or Delrin. Glass, such as Pyrex, for example, may also be used. The sleeve may be made of metal (e.g., stainless steel, aluminum, titanium, brass).

In a specific implementation, the sleeve is frictionally fit over the collar. Sealing members such as one or more O-rings between the sleeve and collar may be used to create a seal between the collar and the sleeve. In another implementation, the collar and sleeve are molded (i.e., integrally molded) as one-piece unit. The collar and sleeve may be glued together using an adhesive.

Although in this specific implementation the sleeve has a circular cross section, it should be appreciated that the cross section can have any shape (e.g., oval, ellipse, square, rectangle, and triangle). In various implementations, the user can select a sleeve having a desired shape to place onto the hand piece. The user can select the shape based on the geometry or contour of the skin to be treated. For example, a sleeve having a rectangular cross section or opening may be used to treat skin areas having tight corners such as the patient's inner thigh.

Figure 6:
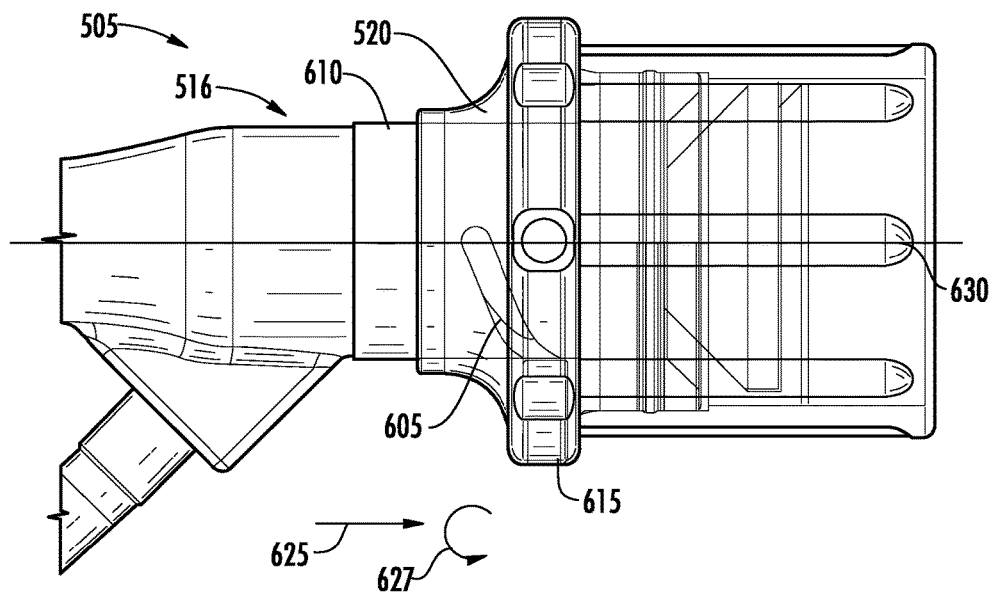
FIG. 6 shows a side view of the hand piece.

FIG. 6 shows a side view of hand piece 505. A first groove 605 is formed in a surface 610 of distal end 516 of the hand piece. A first peg 615 is fitted into a hole in the flange of collar 520 such that an end of the first peg exits an inside surface of the collar. The end of the first peg is received by, engages, or projects into the first groove.

The groove spirals, twists, or at least partially spirals or twists about the distal end. In an implementation, the groove extends in a first direction 625 and a second direction 627. The first direction is parallel to a longitudinal axis 630 passing through the hand piece. The second direction is a radial direction about the longitudinal axis.

The groove may be referred to as a track, guide, channel, flute, slot, furrow, score, kerf, notch, or recess. The groove may be formed using any technique such as machining, milling, carving, engraving, etching (e.g., chemical etching), rifling, or combinations of these. The groove may be formed using a mold or die.

Although FIG. 6 shows one groove, there can be any number of grooves. For example, there can be two, three, four, five, or more than five grooves. A cross-sectional shape of the groove may be a semicircle, square, rectangle, triangle, or any other shape.

The groove receives the end of the peg and provides a path for converting rotational motion of the adjustable tip by the user into linear motion. That is, when the user turns the adjustable tip, the end of peg is constrained or guided by the contours of the groove. The adjustable tip follows the path of the groove because the peg is connected to the adjustable tip. The peg may be referred to as a tab, pin, rod, insert, key, nubbin, or projection.

Figure 7:
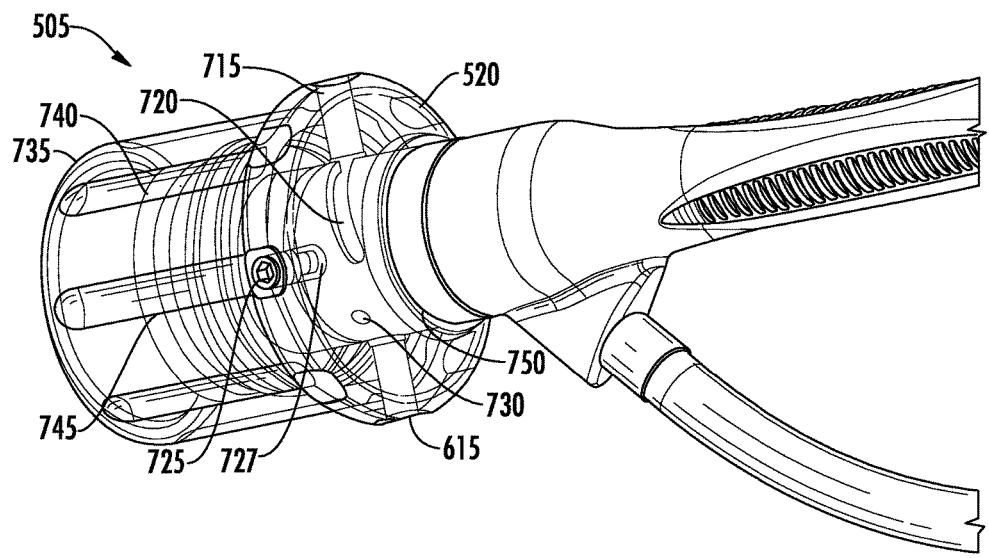
FIG. 7 shows a perspective view of the hand piece from a proximal end of the hand piece.

FIG. 7 shows a perspective view of hand piece 505 from a proximal end of the hand piece looking towards the distal end. In this specific implementation, the hand piece includes an indexing assembly to releasably hold or retain the collar in its user-selected angular position. This specific implementation of the indexing assembly includes a ball detent mechanism. A pin 725 is fitted into a hole in the flange of the collar and a set of detents 730 is formed on the distal end of the hand piece. The detents are radially and axially spaced. That is, the detents are spaced angularly about the handle. The detents are also spaced along a central or longitudinal axis of the handle. The detents help the user to lock or set a position of an opening 735 of the adjustable tip relative to a surface 740 of a treatment head 745.

In a specific implementation, pin 725 of the ball detent mechanism includes a ball or sphere 727 and a biasing member such as a spring to urge the ball into a detent. In this specific implementation, a body of the pin between first and second ends of the pin is bored or hollow. The spring (e.g., compression spring) and ball are placed inside or within the body. The spring urges the ball towards an opening at the second end of the pin such that a portion of the ball extends or protrudes past the opening. A diameter of the opening is less than a diameter of the ball to prevent the ball from falling out of the pin.

As the adjustable tip is rotated the portion of the ball falls into the detent under the spring pressure and the opening of the adjustable tip is at a specific axial position relative to the treatment head. The detent hinders the rotation of the adjustable tip. Additional force or torque applied to the adjustable tip dislodges the ball from the detent. That is, the portion of the ball recedes into the pin opening against the spring pressure. The detent may be referred to as a dimple, depression, indentation, recess, cavity, or stop.

There can be any number of detents. In a specific implementation, a hand piece includes three detents. In another implementation, a hand piece includes one detent. A hand piece may include no detents, 2, 4, 5, 6, 7, 8, 9, 10, or more than 10 detents. Typically, a number of detents is proportional to a size or diameter of the treatment head. In various implementations, a hand piece having a treatment head with a diameter of about 25 millimeters has three detents. A hand piece having a treatment head with a diameter of about 15 millimeters has one detent.

In a specific implementation, the adjustable tip can be rotated so that it can be in a first, second, third, or fourth position relative to the surface of the treatment head. In the first position, a first depth or distance between the adjustable tip opening and the treatment head surface is about 5 millimeters. In this specific implementation, the ball of the detent mechanism is not engaged with or is disengaged from a detent. In another implementation, the ball engages the detent. In the second position, a second distance between the adjustable tip opening and the treatment head surface is about 7 millimeters and the ball of the detent mechanism engages a first detent. In the third position, a third distance between the adjustable tip opening and the treatment head surface is about 9 millimeters and the ball of the detent mechanism engages a second detent. In the fourth position, a fourth distance between the adjustable tip opening and the treatment head surface is about 11 millimeters and the ball of the detent mechanism engages a third detent.

In this specific implementation, the distance between the adjustable tip opening and the treatment head surface ranges from about 5 millimeters to about 11 millimeters. The adjustable tip can be adjusted to one of four discrete positions. However, it should be appreciated that the adjustable tip can be adjusted to any number of discrete positions depending on, for example, the number of detents. The number of discrete positions is proportional to the number of detents.

Furthermore, the adjustable tip may be continuously adjusted. The adjustable tip may be adjusted to any number of intermediate positions between the first and second position, between the second and third position, or between the third and fourth position. For example, a first intermediate position is between the second and third positions. In this first intermediate position, the ball is between the first and second detent and is not engaged with a detent. A first intermediate distance between the adjustable tip opening and the treatment head surface will be greater than 7 millimeters and less than 9 millimeters.

In this specific implementation, the adjustable tip is adjustable in 2-millimeter increments. That is, a difference between a distance from the tip opening to the treatment head at a position of the tip and a next distance from the tip opening to the treatment head at a next position of the tip is about 2 millimeters. However, the difference can be any value (e.g., 1, 2, 3, 4, or 5 millimeters). The difference may be constant or it may vary.

In another specific implementation, the adjustable tip can be rotated so that it can be in a first, second, or third position relative to the surface of the treatment head. In the first position, a first depth or distance between the adjustable tip opening and the treatment head surface is about 3 millimeters. In this specific implementation, the ball of the detent mechanism is not engaged with or is disengaged from a detent. In another implementation, the ball engages the detent. In the second position, a second distance between the adjustable tip opening and the treatment head surface is about 5 millimeters and the ball of the detent mechanism engages a first detent. In the third position, a third distance between the adjustable tip opening and the treatment head surface is about 6 millimeters and the ball of the detent mechanism does not engage a detent. In another implementation, the ball engages a second detent.

The indexing assembly allows the user to set consistently the depths between the tip opening and the treatment head. For example, if patient A prefers a first setting (i.e., a first distance between the tip opening and the treatment head), the user can record that first setting in patient A's medical file. Then, when patient A returns for another treatment, the user can adjust the hand piece to the first setting. In some implementations, the detents are omitted.

The ball detent mechanism is merely one type of an indexing assembly and other types of indexing assemblies may instead be used. Some examples of indexing assemblies include an indexing clutch, ball plunger, indexing ring, or indexing plate (e.g., a plate having a set of preset holes in a backing plate).

Figure 15:
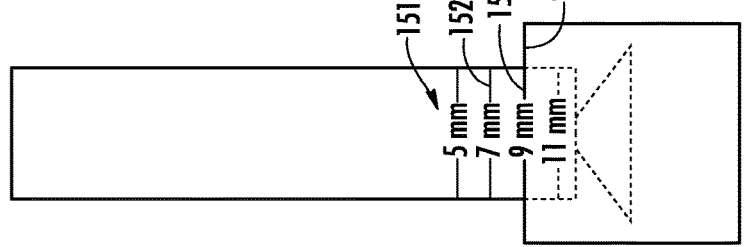
FIG. 15 shows a side view of a hand piece with radial markings.

In a specific implementation, a surface of the distal end includes graduated or radial markings 1510. See FIG. 15. In this specific implementation, the graduated markings include a set of lines circumscribing or at least partially circumscribing the distal end. The set of lines are spaced at predetermined distances along the longitudinal axis of the hand piece. A set of numbers, symbols, characters, or letters may be adjacent or next to the set of lines.

The graduated markings may be made using any technique for making a visible impression on the hand piece. Some examples of techniques include printing, silkscreen printing, masking, stamping, plating, thermography, embossing, painting, engraving, etching, anodizing, oxidizing, deposition, imprinting, and chemical processing.

The graduated markings provide the user with a visual indication of the position of the adjustable tip opening with respect to the treatment head. In an implementation, the graduated markings can indicate a degree of rotation or movement of the adjustable tip about the distal end and therefore the distance between the adjustable tip opening and the surface of the treatment head.

For example, in the first position of the adjustable tip, an edge 1515 of the collar is aligned with a first marking 1520 on the distal end. The first marking indicates to the user that a first distance is between the adjustable tip opening and the surface of the treatment head. In the second position of the adjustable tip, the edge of the collar is aligned with a second marking 1525 on the distal end. The second marking indicates to the user that a second distance, different from the first distance, is between the adjustable tip opening and the surface of the treatment head. In another implementation, the collar includes a window or other opening through which the user can see the graduated markings.

In a specific implementation, the graduated or radial markings include the distance measurements (e.g., 5 millimeters, 7 millimeters, 9 millimeters, and 11 millimeters) between the tip opening and the surface of the treatment head. That is, these radial markings can denote depth and can allow precise adjustment of the distance between the tip opening and the surface of the treatment head. In another implementation, the graduated markings do not include the distance measurements. A hand piece may include the radial markings and no detent mechanism.

Referring now to FIG. 7, this implementation of the hand piece includes an additional peg and groove to help provide a secure attachment of the collar to the handle (i.e., to prevent the collar from wobbling when turned). Similar to first peg 615, a second peg 715 is fitted into a hole in the flange of collar 520. An end of the second peg exits the inside surface of the collar and is received by a second groove 720.

In this specific implementation, the first peg and groove are arranged opposite the second peg and groove. The first peg is opposite or diametrically opposite the second peg. The first groove is opposite the second groove. An angle between the first and second peg or between the first and second groove is about 180 degrees. However, it should be appreciated that any angle can be between the first and second pegs. For example, an angle between the first and second peg or between the first and second groove can be about 30, 45, or 90 degrees. Similarly, any angle can be between the first and second grooves (e.g., 30, 45, or 90 degrees).

Figure 8:
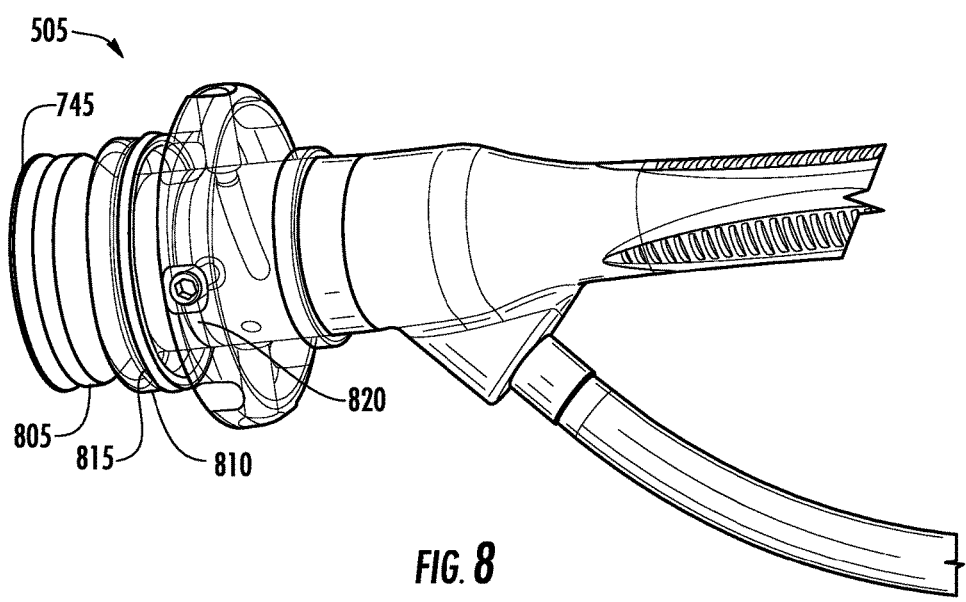
FIG. 8 shows a perspective view of the hand piece with portions of the adjustable tip omitted.

FIG. 8 shows another perspective view of hand piece 505 from the proximal end of the hand piece looking towards the distal end. The sleeve has been omitted from this figure. Treatment head 745 is attached to a treatment head holder 805. The collar includes an extension 810 over which the sleeve is fit. An O-ring 815 is positioned between the extension and sleeve to create a seal. Similarly, an O-ring 820 is positioned between the collar and the distal end of the hand piece to create another seal. The O-ring seals can prevent fluid from leaking out. The seals can also help to maintain the vacuum or suction force in the tip.

Figure 9:
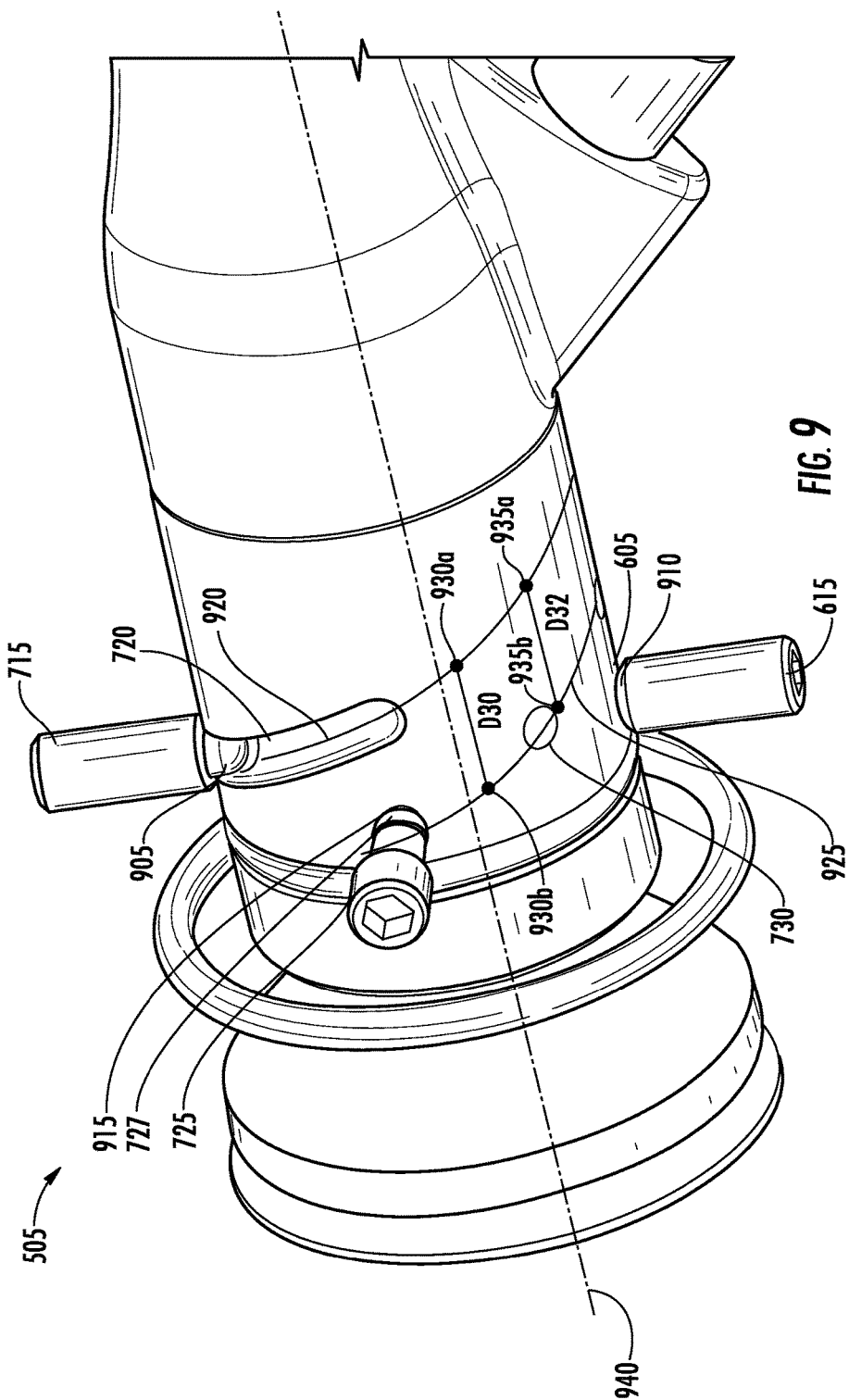
FIG. 9 shows a perspective view of the hand piece's adjustment and positioning mechanism.

FIG. 9 shows another perspective view of hand piece 505 from the proximal end of the hand piece looking towards the distal end. The sleeve and collar have been omitted from this figure. The distal end of the hand piece includes an end 905 of second peg 715 which engages second groove 720. Similarly, an end 910 of first peg 615 engages first groove 605. Pin 725 of the ball detent mechanism includes ball 727. A portion of the ball is received by a first detent 915 in set of detents 730. A first helix 920 follows the first groove. A second helix 925 passes through a reference point of each detent in the set of detents.

The ends of the first and second pegs may be dome shaped as shown in the figure. That is, the ends may be curved or rounded. This allows the pegs to slide smoothly within the grooves. The ends of the pegs can have any shape (e.g., square, rectangle, triangle, or oval). The shape of the ends may be complementary with the cross section of the grooves so that the ends can nest within or fit the grooves.

Each helix may be defined by a curve traced on the surface of the distal end of the hand piece by the rotation of a point crossing its right sections at a constant oblique angle. In a specific implementation, the first and second helixes are the same. For example, the first and second helixes have the same degree of curvature or twist. The first helix is parallel with the second helix. This allows the ball of the detent mechanism to fall into each of the detents as the adjustable tip is rotated about the distal end and along the path defined by the grooves.

In this specific implementation, a first distance D30 is between a first point 930a on the first helix and a second point 930b on the second helix. A second distance D32 is between a third point 935a on the first helix and a fourth point 935b on the second helix. The first and second distances are measured parallel to a longitudinal axis 940 passing through the hand piece. The first and second distances are the same. A line passing through the first and second points is parallel with a line passing through the third and fourth points. The lines are parallel to the longitudinal axis.

In a specific implementation, a groove such as the first groove, second groove, or both does not completely encircle or spiral around the hand piece. In this specific implementation, a line drawn between any two points on the groove does not pass through a center of the hand piece. The line does not intersect the longitudinal axis. In another implementation, the groove completely encircles or spirals around the hand piece. A line drawn between two points on the groove may pass through the center of the hand piece. The line may intersect the longitudinal axis.

Figure 10:
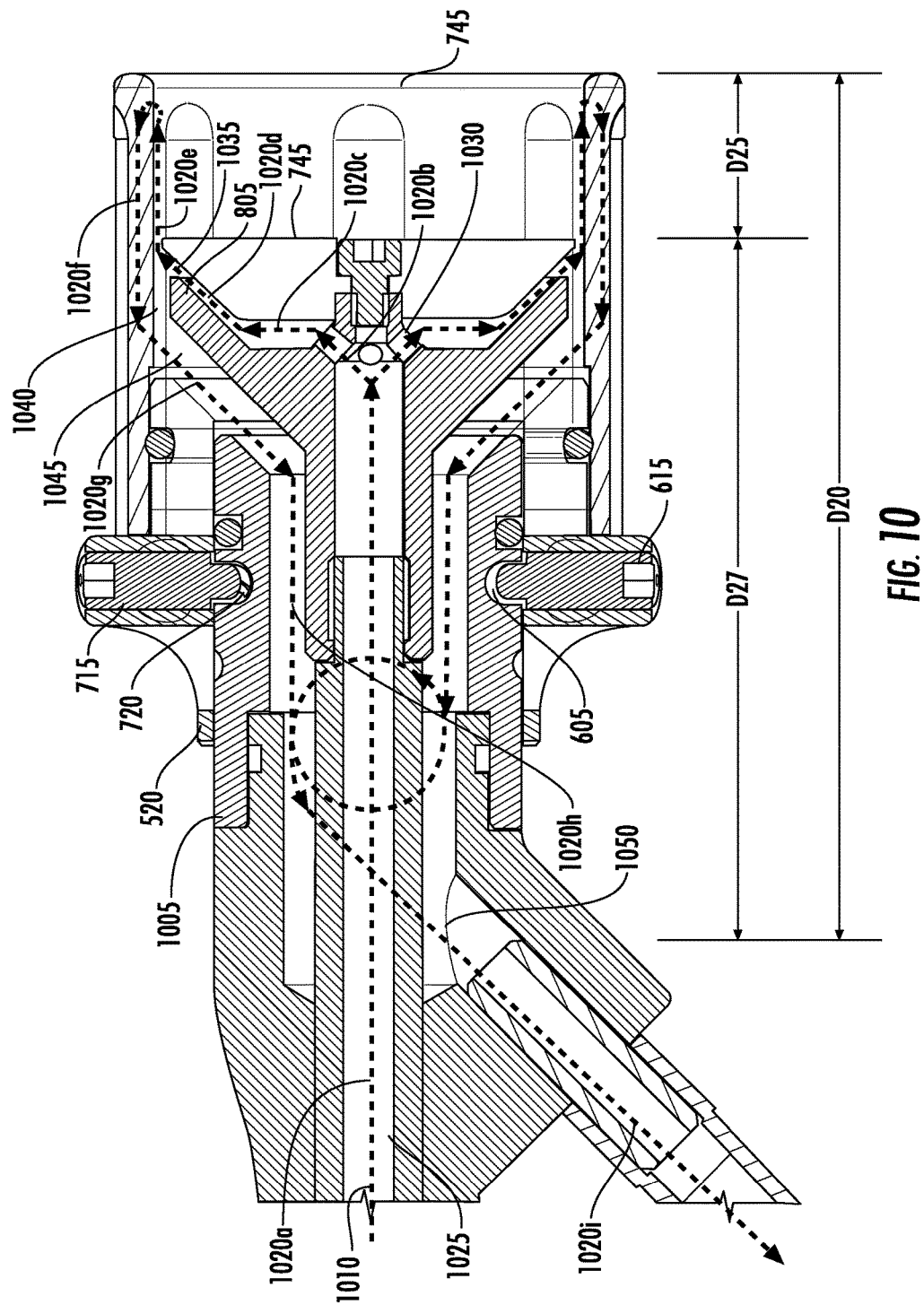
FIG. 10 shows a longitudinal section view of the hand piece and a flow path through the hand piece.
Figure 11:
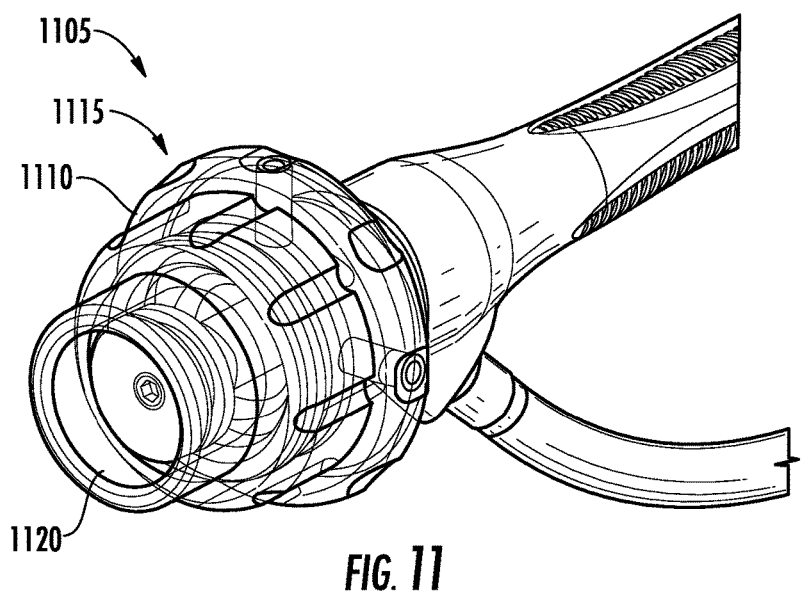
FIG. 11 shows a perspective view of a second embodiment of a skin treatment hand piece with an adjustable tip.
Figure 12:
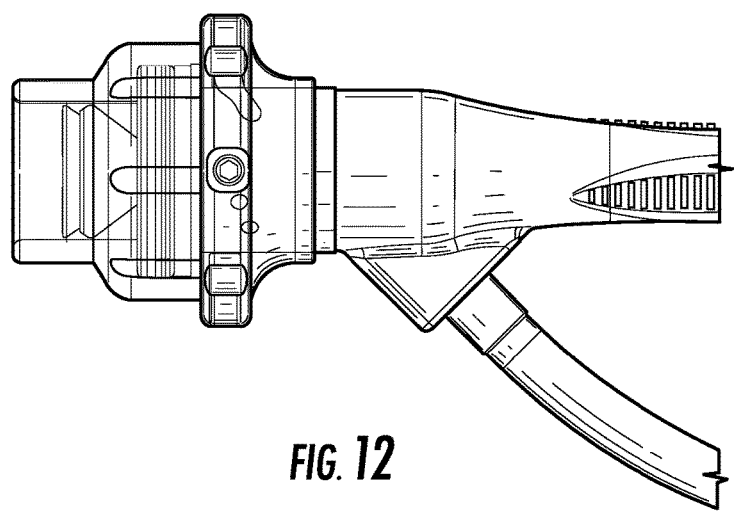
FIG. 12 shows a side view of the hand piece.
Figure 13:
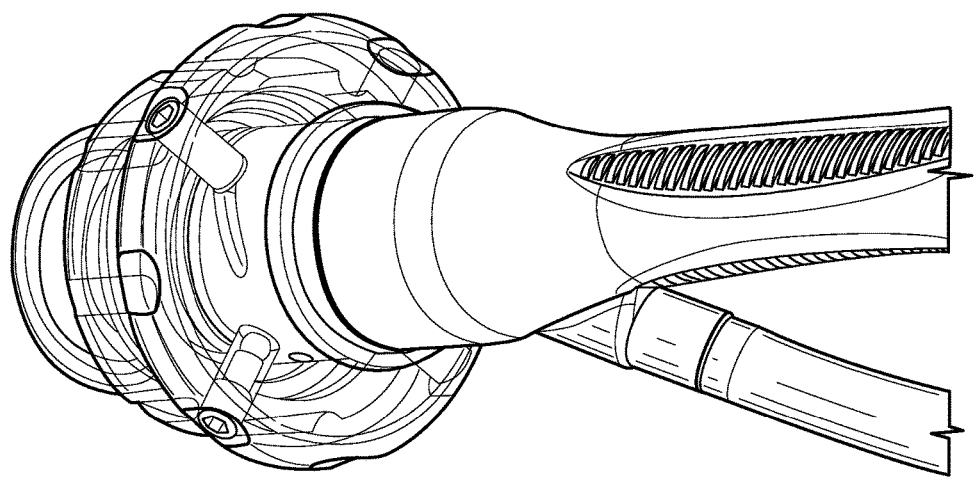
FIG. 13 shows a perspective view of the hand piece from a proximal end of the hand piece.
Figure 14:
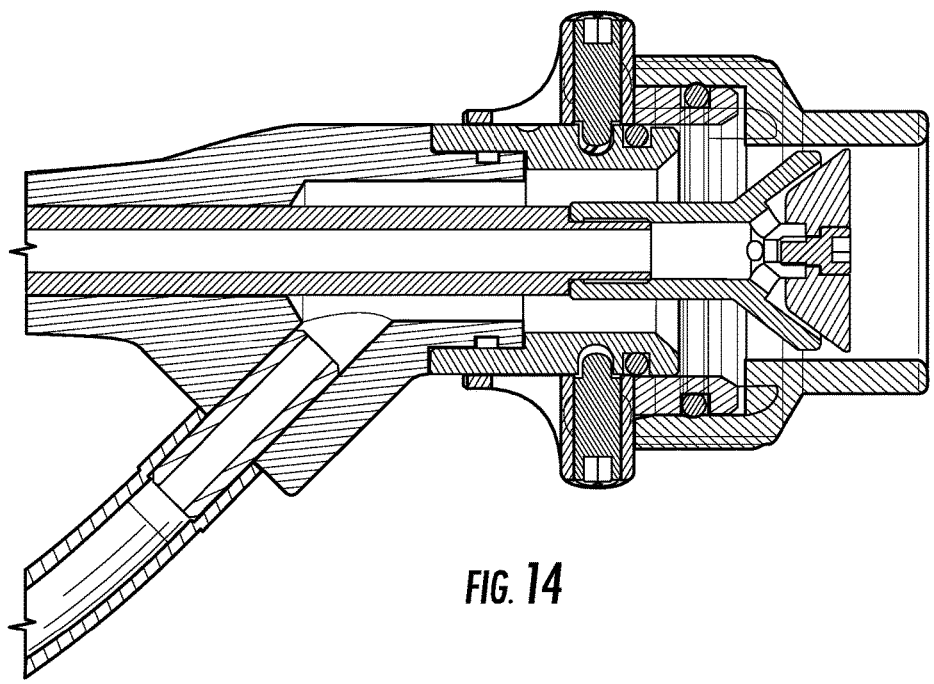
FIG. 14 shows a longitudinal section view of the hand piece.

FIG. 10 shows a longitudinal section of the hand piece. The distal end of the hand piece includes a cannula or end piece 1005 attached to a distal end of the handle. Collar 520 of the adjustable tip is rotatably connected to the distal end of the handle via first and second pegs 615 and 715 whose ends are engaged with first and second grooves 605 and 720, respectively. A flow path or vacuum loop 1010 shows the flow of fluids through the hand piece.

The cannula may be secured to the distal end of the handle using an adhesive such as epoxy, screws, bolts, threads, or any combinations of these. The cannula may be molded with the handle.

The cannula, collar, or both may be made of metal. Some examples of metals include stainless steel, steel, aluminum, titanium, or brass. But, the cannula, collar, or both can be made using any material such as carbon composites, plastics, or ceramics. Some examples of plastics include polyoxymethylene, polyetheretherketone, polyphenylenesulfide, polyethylene terephthalate (PET), other polyesters, polyamides, polyaramids, nylon, polypropylene, thermoplastics, polycarbonate, acrylonitrile, butadiene styrene (ABS), or Delrin.

In a specific implementation, the cannula is made of a material which has greater durability and resistance to wear as compared to the material used to make the collar. That is, the collar may be designed to wear out before the cannula. The cannula may be made of a first type of material such as metal and the collar may be made of a second type of material, different from the first type, such as a plastic. One benefit of this feature is that after the collar wears out due to repeatedly adjusting the tip, the collar may be replaced with a new collar. In another implementation, the cannula and collar are made of the same material. The cannula is designed to wear out before the collar. That is, the collar is made of a material having a greater durability and resistance to wear as compared to the material used to make the cannula.

The cannula, collar, or both may be made using self-lubricating materials. Typically, friction is generated when an inner surface of the collar rubs against the surface of the cannula as the adjustable tip is rotated or otherwise moved. The friction can contribute to wear of the parts. It can be desirable to reduce the friction to increase the life span of the parts. Thus, for example, the collar may be made of a composite including graphite and plastic where there is a greater amount of graphite than plastic. The higher percentage of graphite causes the parts to slip over rather than rub against each other. A self-lubricating material may be bonded to one or more of the parts.

Vacuum source 226 (see FIG. 2) is turned on to establish a vacuum within the system. A closed vacuum loop is formed when opening 745 of the adjustable tip is placed against the patient's skin which seals the opening. A targeted area of the skin is drawn up into the opening and a central portion of the targeted skin is draw into contact with the treatment head (see FIGS. 3-4). Fluids from the fluid reservoir are drawn into the hand piece. The fluids follow the flow path thus treating the skin before being drawn back into the hand piece and into the collection reservoir along with any skin particles and other debris.

More specifically, in a specific implementation, a first segment 1020*a* of the flow path flows through a tubular passageway 1025 in the handle or from a proximal end to a distal end of the handle. The first segment is parallel to the longitudinal axis of the hand piece. One or more portions of the fluid is then diverted into one or more channels 1030 behind treatment head 745. A second segment 1020*b* of the flow path flows into the one or more channels. The second segment is at an angle with respect to the first segment. The angle may be an oblique angle. The angle may be about 5, 10, 15, 20, 25, 30, 35, 40, 45, 50, 55, 60, 65, 70, 75, 80, or 85 degrees. The first and second segments may be perpendicular.

A third segment 1020*c* of the flow path is perpendicular to the first segment. The third segment is parallel to a surface (e.g., abrasive surface) of the treatment head. A fourth segment 1020*d* of the flow path is at an angle with respect to the third segment. The fourth segment of the flow path then flows out of an opening 1035 between the treatment head and treatment head holder 805.

A fifth segment 1020*e* of the flow path is parallel with the first segment. As the hand piece is moved over the patient's skin, the fluid flows around or about a perimeter or circumference of the treatment head and across the surface of the treatment head to treat the patient's skin. In this specific implementation, the fluid does not pass through or flow through the treatment head. The treatment head is made of a nonporous or not permeable material that does not have any openings or pores for fluid to pass through. The treatment head is made of a solid material such as metal which does not absorb or expand when contacted with liquids.

In other implementations, the treatment head has one or more openings for fluid to pass through. For example, there may be an opening in a center of the treatment head that allows fluid to pass through. The treatment head may be made of a porous material such as a sponge. The sponge may be impregnated with abrasive particles.

In a specific implementation, the fluid does not exit or pass through the tip opening. That is, the fluid is contained within the sleeve. The fluid treats the skin within the sleeve and is then drawn back into the hand piece. In another implementation, the fluid or a portion of the fluid exits the tip opening.

After treating the skin, the fluid (i.e., spent fluid), skin particles, and other debris is then drawn into an annular opening 1040. The annular opening surrounds, encircles, or at least partially surrounds or encircles the treatment head. The fluid flows in a direction away from a center of the treatment head. In an implementation, an edge or periphery of the treatment head does not touch an inner surface of the sleeve. Rather, there is a space (i.e., annular opening) between the edge of the treatment head and the inner surface of the sleeve. This space allows fluid, skin particles, and other debris to pass through.

A width of the annular opening is from the edge of the treatment head to the inner surface of the sleeve. In a specific implementation, the width is about 2 millimeters, but may range from about 0.5 millimeters to about 5 millimeters. This includes, for example, about 0.6, 0.7, 0.8, 0.9, 1, 1.1, 1.2, 1.3, 1.4, 1.5, 1.6, 1.7, 1.8, 1.9, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or more than 5 millimeters. The width may be less than 0.5 millimeters.

A greater width allows larger pieces abraded skin particles to pass through without the tip becoming clogged. A smaller width allows for a greater treatment head surface area. The user may select a hand piece or tip having an appropriate width depending upon the application. For example, if the patient has scaly or flaky skin the user may desire to use a hand piece having a large annular opening since it is likely that there will be larger pieces of abraded skin particles as compared to a patient who has normal skin.

A ratio of the diameter of the treatment head to the inner diameter of the sleeve may be about 1:1.16, but may range from about 1:1.01 to about 1:5. Some examples of the ratio include 1:1.05, 1:1.10, 1:1.11, 1:1.12, 1:1.13, 1:1.14, 1:1.15, 1:1.17, 1:1.18, 1:1.19, 1:1.2, 1:1.25, 1:1.3, 1:1.35, 1:1.40, 1:1.5, 1:2, 1:2.5, 1:3, 1:3.5, 1:4, and 1:4.5.

A sixth segment 1020*f* of the flow path is parallel to the first segment, but the segments flow in opposite directions. A seventh segment 1020*g* of the flow path is at an angle with respect to the sixth segment. The seventh segment may be parallel to the second segment, fourth segment, or both. The seventh segment indicates flow through an annular passageway 1045. The annular passageway is connected to the annular opening. The annular passageway may at least partially encircle or surround the treatment head holder. The annular passageway may at least partially encircle or surround the tubular passageway.

An eighth segment 1020*h* of the flow path is at an angle with respect to the seventh segment. The eighth segment is parallel to the first segment, but the segments flow in opposite directions. The fluid flows around or encircles at least a portion of the tubular passageway. A ninth segment 1020*i* of the flow path flows into a vacuum or suction port 1050.

This application describes a specific implementation of the invention where the flow direction is as shown in FIG. 10: the fluid is delivered through the passageway in the hand piece to the tip. This fluid is then vacuumed into the vacuum line through the vacuum port. However, in an alternate embodiment of the invention, the flow direction is opposite of that shown in FIG. 10, where fluid is drawn into the passageway of the hand piece from the vacuum line.

Figure 16:
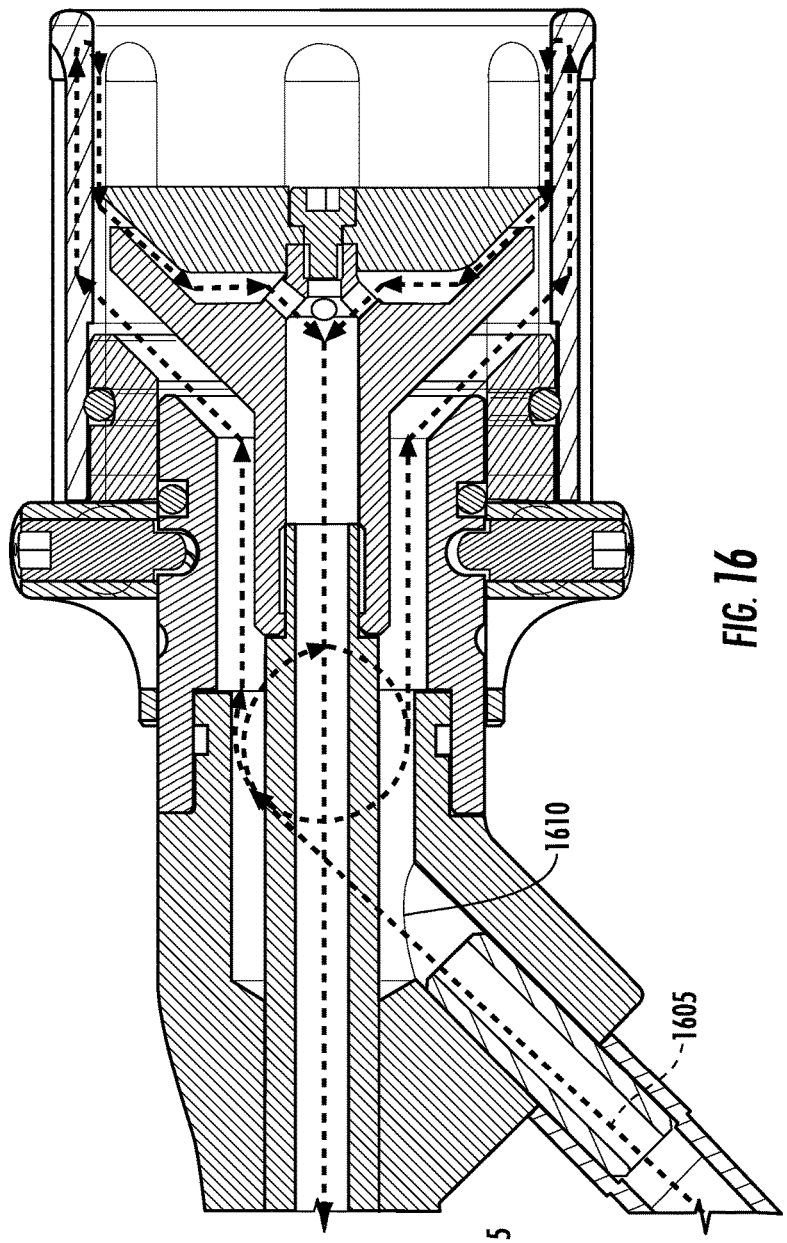
FIG. 16 shows a longitudinal section view of a hand piece having a flow path that is opposite the flow path shown in FIG. 10.

For example, FIG. 16 shows a longitudinal section of the hand piece where a flow path 1605 is opposite of that shown in FIG. 10. In this specific implementation, the fluid is delivered dorsally and the vacuum pressure is delivered axially. That is, the flow path is from a port 1610 located on a side of the hand piece (i.e., between distal and proximal ends of the hand piece). The fluid surrounds at least a portion of the tubular passageway, flows out towards the tip opening at the distal end, and then into the tubular passageway towards the proximal end. This specific implementation positions the suction closer to the skin as compared to the implementation shown in FIG. 10. This can improve upon the reuptake of fluid in the tip when contact with the skin is broken and can help to prevent or minimize drips and the amount of spent fluid and skin debris left on the skin. This specific implementation may be used with large treatment heads (e.g., 25-millimeter diameter heads) where there may be a greater volume of fluid outputted as compared to small treatment heads (e.g., 15-millimeter diameter heads).

An adjustable tip may include one or more fluid channels. For example, FIG. 19 shows a perspective view of an adjustable tip 1905 having a set of fluid channels 1910. The channels are formed on an inside or interior surface or circumference of a sleeve 1915 of the tip and may be distributed evenly about or around a treatment head 1920. The channels extend in a direction perpendicular to a surface of the treatment head or the skin. There can be any number of fluid channels (e.g., 4, 5, 6, 7, 8, 9, 10, or more than 10 fluid channels). A channel may be referred to as a groove, ridge, track, flute, rut, conduit, gutter, or furrow.

The channels are optional and are not included in some implementations of the invention. The channels can be used to facilitate or enhance the hydrodynamics of the fluid. More specifically, the channels can be used to help control or direct the delivery of fluid to the skin, control the pick-up of fluid from the skin, or both. The channels can help prevent the dripping of fluid, such as a fluid including a viscous liquid.

Referring now to FIG. 10, in a specific implementation, the vacuum, fluid flow, or both is adjustable. Changing the position of the tip may the change the amount of vacuum, fluid flow, or both. A volume of the annular passageway may be adjusted by adjusting the adjustable tip. In a specific implementation, the volume is inversely proportional with the distance between the treatment head and the tip opening. In another implementation, the volume is proportional with the distance between the treatment head and the tip opening.

A distance D20 from the suction port to the tip opening is greater than a distance D25 from the treatment surface to the tip opening. A distance D27 between the suction port and treatment surface remains fixed as a position of the treatment surface relative to the tip opening is altered.

In this specific implementation, the tubular passageway, annular passageway, annular opening, and treatment head are concentric. In another implementation, various combinations of the tubular passageway, annular passageway, annular opening, or treatment head are not concentric.

FIGS. 11-14 show a second embodiment of a hand piece 1105. This hand piece is similar to the hand piece shown in FIGS. 5-10, but this hand piece includes a treatment head having a diameter of about 15 millimeters. The diameter of the treatment head shown in FIGS. 5-10 is about 25 millimeters. Furthermore, a sleeve 1110 of an adjustable tip 1115 has a first opening 1120 which is smaller than the opening in sleeve 530 (see FIG. 5).

Typically, the first opening of the sleeve is proportional to the surface area or diameter of the treatment head. In this specific implementation, first opening 1120 has an inside diameter of about 19 millimeters. The diameter can vary widely depending upon the application. The sleeve has a second opening, opposite the first opening. The second opening allows the sleeve to be fit over the sleeve of the collar. The diameter of the second opening of sleeve 1110 is greater than the diameter of the first opening.

In a specific implementation, a user can replace the sleeve and treatment head with another sleeve and treatment head having a different size (i.e., diameter). Thus, a user can have a hand piece with a first treatment head and sleeve. The first treatment head has a first diameter. The first sleeve has a first opening and a second opening, opposite the first opening. Diameters of the first and second openings are the same. The second opening is fit over the sleeve of the collar. A flow to replace the first treatment head and sleeve may be as follows:

1. Remove first treatment head and sleeve from hand piece.

2. Attach a second treatment head having a second diameter, different from the first diameter, to the hand piece.

3. Slip a second sleeve onto the hand piece. The second sleeve has a third opening and a fourth opening, opposite the third opening. Diameters of the third and fourth openings are different. The diameter of the fourth opening is the same as the diameter of the second opening of the first sleeve. This allows the second sleeve to similarly fit over the collar.

In another implementation, a hand piece is not designed to allow a user to replace a treatment head with another treatment head having a different diameter. In this specific implementation, the user can replace treatment heads having different levels of abrasiveness, but the same diameter.

The treatment head can be of any size (i.e., surface area) or diameter. The diameter of a treatment head can range from about 3 millimeters to about 75 millimeters. This includes, for example, 5, 6, 9, 10, 15, 20, 30, 35, 40, 45, 50, 55, 60, or 70 millimeters, or more than 75 millimeters. A treatment head can have a diameter that is less than 5 millimeters. Smaller diameter treatment heads can be used to treat smaller areas such as a patient's forehead or cheek. Larger diameter treatment heads can be used to treat larger areas such as a patient's torso or back.

In a specific implementation, the treatment head has an abrasive surface. The abrasive surface may be formed by fusing (e.g., gluing, imbedding) abrasive particles to the surface. The abrasive surface may also be formed by applying an adhesive-backed paper substrate to the surface, knurling, machining, laser treatment or otherwise mechanically or chemically treating the surface. The abrasive surface may also include an abrasive open screen with bonded abrasive particles.

In this specific implementation, the abrasive particles are diamonds. Other examples of abrasive particles include silicone carbide, magnesium oxide, carborundum, aluminum oxide, sodium bicarbonate, and the like. These abrasive particles may be used individually or in combination.

The abrasive particles are generally of a size (i.e., grit size) ranging from about 50 grit to about 300 grit, including for example, 30, 60, 80, 100, 120, and 140 grit. The coarser particles (at the lower ends of the grit ranges) may be provided for use in initial treatments, while finer particles (at the higher ends of the grit ranges) may be employed for later treatments. A treatment head having a 30-grit abrasive surface may be referred to as coarse. A treatment head having a 30-grit abrasive surface may be referred to as "coarse." A treatment head having a 60-grit abrasive surface may be referred to as "medium coarse." A treatment head having an 80-grit abrasive surface may be referred to as "medium." A treatment head having a 100-grit abrasive surface may be referred to as "medium fine." A treatment head having a 120-grit abrasive surface may be referred to as "fine." A treatment head having a 140-grit abrasive surface may be referred to as "extra-fine."

In another implementation, a treatment head has a smooth surface and does not have abrasive particles such as diamonds. This treatment head can be used where the user desires to provide a small amount of exfoliation and a large amount of infusion of solution. In this specific implementation, the exfoliation is provided by the vacuum and not the surface of the treatment head. The treatment head having the smooth surface can be used to treat the lips, delicate areas around the eyes, areas that are inflamed, and sensitive postsurgical skin.

A treatment head having a smooth surface may be used to provide a vacuum-massage. This treatment head may be referred to as a massage plate or adjustable depth massage plate and may be used during a vacuum-based cellulite or body treatment with simultaneous irrigation and lubrication of the skin or tissue by therapeutic agents. The massage plate may be planar or flat. The massage plate may instead include bumps, nodes, lumps, or the like formed on a surface or tissue-facing surface of the plate. During a skin treatment session, these features on the surface of the massage plate can help to relax the body and increase blood flow to the tissue.

The treatment head may be made of metal (e.g., stainless steel, surgical stainless steel, aluminum, titanium, brass) or plastic such as nylon, thermoplastics, polyethylene, polycarbonate, acrylonitrile butadiene styrene (ABS), or Delrin. Glass, such as Pyrex, for example, may also be used.

In a specific implementation, the surface of the treatment head is flat, planar or substantially planar. However, in other implementations, a treatment head is nonplanar. For example, a treatment head may have a curved, rounded, or spherical surface. A treatment head may include groups of bristles such as those discussed in U.S. patent application Ser. No. 12/040,867 which is incorporated by reference.

A user can purchase a skin treatment kit. In an implementation, the kit includes first and second hand pieces. The first hand piece is designed for treatment heads with 25-millimeter diameters. This hand piece may be used on the patient's back, buttocks, torso, or thighs. The second hand piece is designed for treatment heads with 15-millimeter diameters. This hand piece may be used on the patient's arms, calves, or other parts of the body with small surface areas. A first set of 25-millimeter diameter treatment heads includes four treatment heads—fine, medium, and coarse diamond treatment heads and a smooth treatment head. A second set of 15-millimeter treatment heads includes four treatment heads—fine, medium, and coarse diamond treatment heads and a smooth treatment head.

In this implementation, the kit further includes a set of lotions of a first type (e.g., a clarifying infusion), a set of lotions of a second type (e.g., a hydrating infusion), and a tray for holding the hand pieces and treatment heads. The set of lotions may be packaged in 177 milliliter (6 ounce) bottles. Each set of lotions may include six bottles.

It should be appreciated that the various components of the kit may be available in any combination and with any number of components. For example, a kit may include treatment heads and no hand pieces and no lotions.

A representative flow for making a hand piece having an adjustable tip is outlined in steps 1 to 6 below.

1. Provide an end piece for a distal end of the hand piece.
2. Machine a first groove (e.g., helical groove) on a surface of the end piece.
3. Machine one or more detents on the surface of the end piece.
4. Place an adjustable tip on the end piece.
5. Insert a peg into the adjustable tip such that an end of the peg engages the first groove.
6. Insert a ball of a ball detent mechanism into the adjustable tip.

Although the steps above are listed in a specific order, the steps may take place in any order, as desired and depending on the specific application. There may be additional or other steps, which may replace one or more of the above steps. Certain steps may be repeated. Certain steps may be omitted. For example, in a specific implementation, the hand piece does not include detents and steps 3 and 6 are omitted.

In step 1 of the flow, an end piece for a distal end of the hand piece is provided. This is the part that the adjustable tip will rotate about. In a specific implementation, this piece is a cylinder. Features to facilitate the adjustment of the hand piece will be formed (e.g., milled or machined) on a cylindrical surface of the cylinder.

In step 2, a first groove (e.g., helical groove) is machined on the cylindrical surface of the end piece. The helical groove may be machined using a milling machine. The end piece is held in a fixture or clamp such as a dividing head, spiral head, or index head of the milling machine. The fixture can rotate the end piece about a longitudinal axis of the end piece. The fixture, in turn, may be mounted to a table of the milling machine. The table can move the end piece longitudinally past a revolving cutter of the milling machine.

The end piece is moved (i.e., feed or advanced) longitudinally past the revolving cutter. At or about the same time, the end piece is rotated about its longitudinal axis. The rate at which the end piece moves longitudinally and rotates may be constant. The helical groove will then be milled on the cylindrical surface of the cylinder. A lead (L) or distance that the helical groove advances longitudinally in one revolution depends on the ratio between the speed of rotation and the longitudinal feeding movement. If the speed of rotation is increased, the lead will be reduced, and vice versa, provided the rate of the lengthwise travel remains the same.

In a specific implementation, the end piece is rotated less than 360 degrees. That is, the end piece does not make a complete revolution. For example, the end piece may be rotated about 10, 20, 30, 40, 50, 60, 70, 80, 90, 100, 110, 120, 130, 140, 150, or 160 degrees or more than 160 degrees. The end piece may be rotated less than 10 degrees. In this specific implementation, the lead of the helical groove is a portion of the lead for one revolution. In another implementation, the end piece is rotated 360 degrees or more than 360 degrees.

A second groove may be machined on the end piece using a similar procedure described above. That is, the second groove may be machined at the same speed of rotation and rate of longitudinal movement used to machine the first groove. The position of the second groove may or may not be diametrically opposite the first groove.

In step 3, one or more detents are machined on the cylindrical surface of the end piece. Typically, the one or more detents are machined using the same speed of rotation and rate of longitudinal movement used to machine the grooves. For example, a first detent is machined at a first position on the cylindrical surface of the end piece. The end piece is rotated and advanced at the same rate used to machine the groove. The rotation is paused before the rotation is complete. A second detent is machined at a second position. This process may be repeated as desired. This helps to produce a set of detents having the same helical path as the grooves.

In step 4, an adjustable tip is placed on the end piece. In a specific implementation, the adjustable tip is frictionally fit over the end piece. Other mechanical attachment mechanisms may instead or additionally be used. Some examples of these attachment mechanisms include twisting and locking, snap-fit, threading, and so forth.

In step 5, a peg is inserted into a hole on the adjustable tip such that an end of the peg protrudes past an inner surface of the adjustable tip and engages the helical groove. This allows the adjustable tip to follow or trace the path of the helical groove when the adjustable tip is rotated. In a specific implementation, the peg is frictionally fit into the hole. The peg may instead or additionally be screwed into the hole. This allows the peg to be unscrewed and the adjustable tip removed for cleaning or replacement.

In step 6, a ball of a ball detent mechanism is inserted into a hole in the adjustable tip. The hole is drilled so that it aligns with the one or more detents as the adjustable tip is rotated.

It should be appreciated that principles of the invention may be implemented using other mechanical arrangements. For example, the grooves, detents or both may instead or additionally be machined onto the adjustable tip. The detents may be machined within the grooves. In various implementations, a linear gear or longitudinal track or rail is used to allow translation or axial displacement of the adjustable tip opening relative to the treatment head. In this specific implementation, the adjustable tip does not rotate. Rather, the adjustable tip moves back and forth along an axial direction without any rotation. In another implementation, a ratchet mechanism including a ratchet gear with gear teeth and a spring-loaded pawl is used to allow rotation of the adjustable tip about the handle and locking of the adjustable tip in a desired position. Ball bearings, needle bearings, bushings, or combinations of these are provided between the adjustable tip and handle to facilitate movement (e.g., rotation or translation).

As another example, the detent mechanism and grooves or helical grooves shown in FIG. 7 are replaced with threads (e.g., screw threads or thread teeth). In this specific implementation, the adjustable tip includes first thread teeth (e.g., female or internal threads) that engage or mesh with second thread teeth (e.g., male or external threads) formed at the distal end of the handle. The depth is adjusted via a screwing motion of the adjustable tip relative to the handle. This specific implementation can allow for precise adjustment of the depth.

In a specific implementation, a first tip that provides a first distance between the tip opening and the treatment head may be swapped with a second tip that provides a second distance, different from the first, between the tip opening and the treatment head.

For example, the user can vary the distance between the tip opening and the treatment head by swapping extensions having the desired length. A first sleeve has a first end, a second end, opposite the first end, and a first tip opening at the first end. A first length is between the first and second ends. When the first sleeve is placed on the hand piece a first depth is between the first tip opening and a treatment head.

A second sleeve has a third end, a fourth end, opposite the third end, and a second tip opening at the third end. A second length is between the third and fourth ends. The second length is different from the first length. That is, lengths of the first and second extensions are different. A user can swap the first sleeve with the second sleeve. That is, the user can pull, twist-off, snap-off, unlock, or otherwise remove the first sleeve from the hand piece and place the second sleeve onto the hand piece. Then, a second depth between the second tip opening and the treatment head will be different from the first depth.

If the second sleeve is longer than the first sleeve (i.e., second length is greater than first length), the second depth will be greater than the first depth. If the second sleeve is shorter than the first sleeve (i.e., second length is less than first length), the second depth will be less than the first depth.

In another specific implementation, a sleeve includes one or more modules or cylinders. Modules can be stacked together to create a sleeve having any length. To make a longer sleeve, a first module can be attached to a second module. To make a shorter sleeve, the second module can be removed from the first module. Lengths or heights of the modules may be the same or different. Any mechanism may be used to connect the modules together. For example, the first and second modules may include threads and thread teeth so that the first and second modules can be screwed together. The first and second modules may snap together. The first and second modules may be press fitted together.

In another specific implementation, the distance between the tip opening and the treatment head is adjusted using spacers or washers. For example, spacers may be placed behind the treatment head or between the treatment head and the treatment head holder to vary the distance between the tip opening and the surface (i.e., abrasive or tissue-facing surface) of the treatment head. That is, the user can remove a treatment head from the hand piece and remove and insert spacers as necessary to achieve the desired distance between the treatment head and the tip opening. In this specific implementation, a first spacer is between a treatment head and a treatment head holder. A depth is from a tip opening to the treatment head. The depth can be increased by adding a second spacer between the treatment head and the treatment head holder, replacing the first spacer with a third spacer having a greater thickness than the first spacer, or both. The depth can be decreased by removing spacers, replacing a spacer with a shorter or thinner spacer, or both.

These spacers may be included with an adjustable-depth microdermabrasion kit. In this specific implementation, the kit includes a microdermabrasion hand piece and a spacer container. The container includes a number of treatment head spacers. The spacers are designed to be placed behind the treatment head. When a first spacer is placed behind the treatment head, there is a first depth from the tip opening to the treatment head. When a second spacer is placed behind the treatment head, there is a second depth, different from the first depth, from the tip opening to the treatment head.

Thicknesses of the first and second spacer may be the same or different. The spacers may be labeled so that the user can identify the thickness of a spacer. The spacers may be color-coded where a color indicates a thickness of a spacer. For example, a blue colored spacer may indicate a spacer having a thickness of about 4 millimeters. A green colored spacer may indicate a spacer having a thickness of about 7 millimeters. A diameter of a spacer may be less than a diameter of the tip opening. A diameter of a spacer may be less than or equal to a diameter of the treatment head.

The distance between the tip opening and the treatment head may be adjusted using treatment heads having varying thicknesses. For example, a first treatment head has a first thickness. A second treatment head has a second thickness, different from the first thickness. A hand piece with the first treatment head has a first distance from a tip opening to the first treatment head. The first treatment head can be replaced with the second treatment head so that there is a second distance, different from the first distance, between the tip opening and the second treatment head.

The various ideas and concepts presented in this application may be combined, in any combination, with other ideas and concepts presented in this application. For example, the discussion of a hand piece having a tip that can be twisted is applicable to the discussion of a tip with a modular tip sleeve piece.

A hand piece of the invention may be combined with other treatment techniques. For example, a hand piece having an adjustable tip may further include LEDs for light or photomodulation therapy, electrodes for delivering radio frequency therapy, a vibrating mechanism for massage therapy, or combinations of these. A hand piece may be used to provide electromagnetic radiation (EMR), ultraviolet light (UV), or light therapy. During a skin treatment session, a hand piece can deliver therapeutic UV light to an area of psoriasis or eczema while simultaneously removing the scale and delivering a therapeutic solution.

Figure 17:
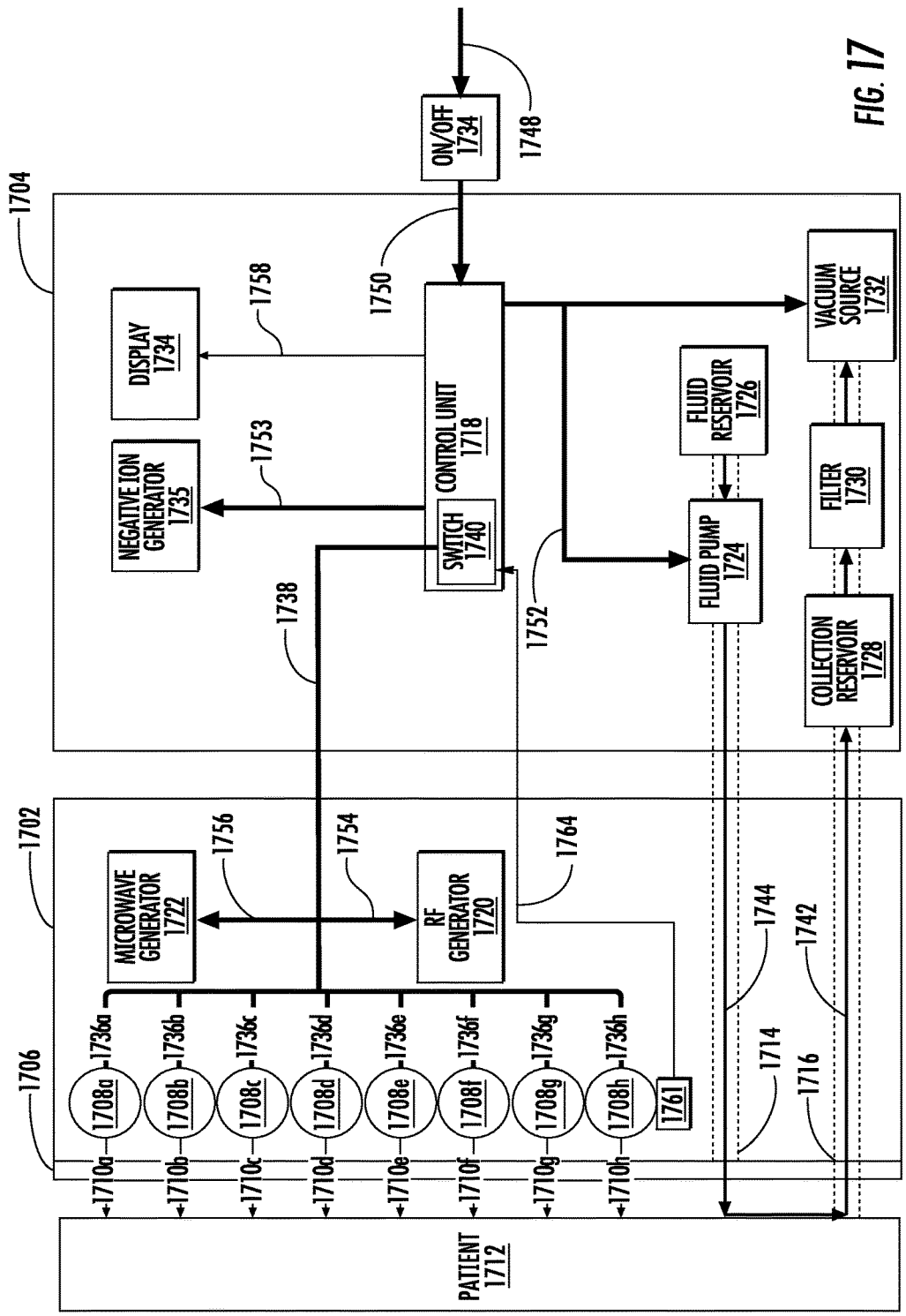
FIG. 17 shows a block diagram of a hand piece having radiation sources.

FIG. 17 shows a block diagram of a hand piece 1702 and console 1704 that includes radiation sources. A tip 1706 attached to the hand piece may include a smooth or abrasive treatment head. This hand piece includes one or more radiation sources or emitters 1708a, 1708b, 1708c, 1708d, 1708e, 1708f, 1708g, and 1708h which emit radiation 1710a, 1710b, 1710c, 1710d, 1710e, 1710f, 1710g, and 1710h into a patient's 1712 skin. The hand piece also includes a fluid delivery line 1714 and a vacuum line 1716. In a specific embodiment, the hand piece includes a microwave generator 1722, a radio frequency (RF) generator, or both. The microwave generator, RF generator, or both is optional and is not present in some implementations of the invention.

The console includes a control unit 1718, a fluid pump 1724, a fluid reservoir 1726, a collection reservoir 1728, a filter 1730, a vacuum source 1732, and a display 1734. In a specific implementation, the console also includes a negative ion generator 1735. Via an on-off switch 1734, power is supplied to the various components in the console such as the fluid pump, vacuum source, and negative ion generator.

Cables 1736a, 1736b, 1736c, 1736d, 1736e, 1736f, 1736g, and 1736h connect each radiation source 1708a, 1708b, 1708c, 1708d, 1708e, 1708f, 1708g, and 1708h, respectively, to a cable 1738 which is then connected to a switch 1740 in the control unit.

The system has a vacuum path 1742 that passes through the vacuum line. The vacuum path includes the vacuum source, which is connected to the filter, which is connected to the collection reservoir. The filter is optional and is not present in some implementations of the invention. The collection reservoir is connected to the hand piece.

The system has a fluid path 1744 that passes through the fluid delivery line. The fluid path includes the fluid reservoir, which is connected to the fluid pump, which is connected to the hand piece. The fluid pump is optional and is not present in some implementations of the invention; in such a case, the fluid is drawn through the fluid path, through the hand piece, to the collection reservoir by the vacuum source. A fluid may include a gas or liquid, or both.

The system has a power path to distribute power (e.g., AC or DC, or both) to the components of the system. Power is supplied to the system through a power input line 1748 to the on-off switch. From the on-off switch, power is supplied via a line 1750 to the control unit.

From the control unit, power is supplied via a line 1752 to the vacuum source and fluid pump. Power is supplied via a line 1753 to the negative ion generator. When power is supplied as AC power (e.g., from an AC outlet), and a component such as the control unit uses DC power, the system will include an AC-to-DC converter to convert AC power to DC power.

From the control unit, power is supplied via cable 1738 to the electrical components in the hand piece such as the radiation sources, the microwave generator, and the RF generator. A line 1754 connects the RF generator to cable 1738. A line 1756 connects the microwave generator to cable 1738. Lines 1754 and 1756 supply power to the RF generator and microwave generator, respectively.

The radiation sources may emit radiation at various wavelengths. The radiation may be emitted as, for example, acoustic waves, radio frequency (RF) waves, microwaves, infrared, far-infrared, near-infrared, visible light, ultraviolet light, far-ultraviolet light, near-ultraviolet light, and combinations of these.

In a specific implementation, one or more radiation sources emit visible light. Visible light is generally electromagnetic radiation having a range of wavelengths from about 380 nanometers to about 750 nanometers.

In some applications it may be desirable to direct a single band or selected multiple bands of visible light waves into the patient's skin. Thus, in a specific implementation, the radiation sources include light emitting diodes (LEDs) which emit a predominately blue light, red light, yellow light, green light, or combinations of these. The radiation sources may include light having a luminance (candela per square meter) that may be two, three, four, or more than four times greater than the ambient light.

Blue light is typically light having a predominate wavelength of about 470 nanometers, but may range from about 450 nanometers to about 495 nanometers. Red light is typically light having a predominate wavelength of about 640 nanometers, but may range from about 620 nanometers to about 750 nanometers. Yellow light is typically light having a predominate wavelength of about 590 nanometers, but may range from about 570 nanometers to about 590 nanometers. Green light is typically light having a predominate wavelength of about 510 nanometers, but may range from about 510 nanometers to about 570 nanometers.

These particular wavelengths of light may be used to treat a variety of skin conditions by transmitting the light into the patient's skin. For example, blue light may be transmitted into the patient's skin in order to treat acne. Red light may be transmitted into the patient's skin to reduce pigmentation and lighten the skin. Yellow light may be transmitted into the patient's skin to promote the production of collagen which reduces fine lines and wrinkles.

In a specific embodiment using LEDs as radiation sources, all of the LEDs emit the same color light. Such an embodiment may be used to provide a focused treatment of a specific skin condition. For example, a teenager with acne problems may undergo treatment with only blue light. These patients, because of their young age, may not yet have the fine lines and wrinkles associated with older patients.

In another embodiment, two or more LEDs simultaneously emit light of different colors which, when combined, create another color of light. For example, a first LED may emit green light. A second LED may emit red light. An implementation of the invention may then include a light mixer to combine the green and red light beams to produce yellow light. It should be appreciated that the light mixer may be used to combine the primary light colors of red, green, and blue in specific ratios to produce a light beam of any color.

In yet another embodiment using LEDs, two or more LEDs emit light of different colors to treat a combination of skin problems. For example, radiation sources 1708a, 1708b, and 1708c may emit blue light. Radiation sources 1708d, 1708e, and 1708f may emit red light. Radiation sources 1708g and 1708h may emit yellow light. Such an embodiment may be appropriate for an older adult who suffers from adult acne in addition to pigmentation, fine lines, and wrinkles.

Emitting or transmitting light at different wavelengths (i.e., different colors) also allows, directing treatment to a specific layer of skin (e.g., epithelium, basement membrane, dermis, and subcutis). For example, longer wavelengths of light, such as red light penetrate deeper into the skin than shorter wavelengths of light such as blue light.

LEDs are just one example of a radiation source that may be used in an implementation of the invention. In other embodiments of the invention, other types of light sources may be used instead, or additionally. Some examples of a radiation source include a light emitting polymer (LEP), organic light emitting diode (OLED), organic electro-luminescence (OEL) device, superluminescent diode (SLD), edge emitting LED (EELED), surface emitting LED (SELED), laser, laser diode, waveguide laser diode, vertical-cavity surface-emitting laser (VCSEL), fiber laser, fluorescent solid state source, lamp, fluorescent lamp, dichroic lamp, incandescent light bulb, halogen light bulb, xenon light bulb, high intensity discharge lamp, and the like.

It should be appreciated that directing a single color light or selected multiple colors of light into the patient's skin may be accomplished in a variety of ways. One embodiment of the invention includes single color LEDs (e.g., blue, red, green, and yellow LEDs). Another embodiment of the invention includes LEDs capable of producing multiple colors. In yet another embodiment, a broad band radiation source is included with an optical element to filter out unwanted wavelengths.

For example, an embodiment of the invention may include one or more light filters through which the light is transmitted before the light is transmitted into the patient's tissue. For example, the tip may include a light filter that is placed over a radiation source. The light filter may be designed with a shape (e.g., annular shape) so that it can be fit over the radiation sources while still allowing the tip, and fluid and vacuum passageways to be exposed. A release mechanism (e.g., release tab) may be included with the radiation source structure holder so that the user can easily remove and replace the light filter.

Such light filters may be used to absorb some wavelengths of light while allowing other wavelengths of light to pass through and into the patient's tissue. For example, a radiation source may be a light bulb that emits white light. White light is composed of all three primary colors (i.e., red, green, and blue). A colored filter may then be used to produce different colors of light.

For example, white light may be transmitted through a red filter to produce red light. That is, a red filter absorbs blue and green light and lets red light pass. White light may be transmitted through a blue filter to produce blue light. That is, a blue filter absorbs red and green light and lets blue light pass. White light may be transmitted through a yellow filter to produce yellow light. That is, a yellow filter absorbs blue light and permits green and red light to pass. The combination of green and red light produces yellow light.

Some examples of filters that may be used in an implementation of the invention include absorptive, dichroic, monochromatic, infrared, ultraviolet, longpass, shortpass, bandpass, and polarization filters.

In other embodiments, a lens may be placed over one or more radiation sources to magnify or focus the radiation emitted by one or more radiation sources. A lens may also be used to protect the radiation sources from damage (e.g., fluid damage). The lens may be designed with a shape (e.g., annular shape) so that it can be fit over the radiation sources while still allowing the tip, and fluid and vacuum passageways to be exposed. A release mechanism (e.g., release tab) may be included with the radiation source structure holder so that the user can easily remove and replace the lens. In some cases it may be desirable to use the lens to magnify the radiation emitted by the radiation sources to provide an effective treatment. However, in other cases, it may instead be desirable to lessen the radiation as may be the case where the patient has sensitive skin. Thus, an embodiment may also include a lens which diverges or attenuates the radiation emitted by one or more radiation sources.

In a specific implementation, one or more optical wave guides, such as optical fiber may be used to transmit light into the patient's tissue. For example, the radiation sources (e.g., LEDs, light bulbs, laser diodes, and the like) may be located in the console as opposed to the hand piece as shown in FIG. 17. Optical fiber may then be used to transmit light from the console to the hand piece. That is, the tip of the hand piece may include one or more ends of optical fiber. The opposite of ends of the optical fiber may then be coupled to the light sources in the console.

In yet another implementation, the radiation sources may be at a different location in the hand piece instead of at the tip as shown in FIG. 17. For example, the radiation sources may be located in the hand piece at the opposite end of the tip.

A benefit of using fiber optics is that the cables do not have to include electrical wiring. That is the cables may be passive as opposed to active. This may then, for example, lessen the chances of a shock hazard to the patient and user.

However, locating the radiation sources at the tip may be beneficial in certain applications. For example, there may be less attenuation of the emitted light as the light does not have to travel from the console to the tip.

In yet another implementation, there may be a combination of LEDs and fiber optic cable ends at the tip. For example, a light therapy treatment may include passing light through a patient's skin at different depths. Thus, light from LEDs in the hand piece may be used to penetrate the patient's skin at a deeper depth than light from fiber optic ends in the hand piece.

In a specific implementation, one or more radiation sources are used to therapeutically heat the patient's tissue. The radiation sources may output radiation that has a power or energy level that may be two, three, four, or more than four times greater than the ambient radiation. The heat may be used to degrade the collagen in the tissue. This causes the tissue to shrink and results in the tightening of the skin and reduction of wrinkles. The radiation sources may deliver RF energy, microwave radiation, or both to the patient's skin.

Thus, in a specific embodiment, the radiation sources may include radio frequency electrodes. The electrodes may be in a monopolar configuration, bipolar configuration, or both. Monopolar configurations typically provide a greater depth of RF energy penetration into the tissue, than bipolar configurations. Monopolar configurations typically penetrate to a depth of about 4 millimeters. Bipolar configurations typically penetrate to a depth of about 0.2 millimeters to about 0.3 millimeters. Some implementations may include only bipolar configurations. Because the bipolar configuration penetrates the tissue to a lesser depth than the monopolar configuration, there is less potential for injury to other structures below the skin such as nerves.

The radiation sources, i.e., electrodes, transmit energy to the tissue via radio frequency waves generated by the RF generator. The control unit allows a user to control the RF parameters, such as power level, cycles, and other parameters, such as selecting pulsed RF waves or continuous RF waves.

The radio frequency waves are typically in the range from about 100 kilohertz to about 450 kilohertz. This includes for example, less than 100 kilohertz, 125, 150, 175, 200, 225, 250, 275, 300, 325, 350, 375, 400, 425, or greater than 450 kilohertz.

The electrodes are typically constructed of materials having a high thermal conductivity such as metals. The metals may include stainless steel, tungsten, brass, beryllium, copper, and the like.

In an embodiment using RF energy, the fluids exiting the tip may serve as a conductive fluid (e.g., saline solution) to conduct RF energy to the skin and ensure electrical contact of the electrode with the skin. The fluids may also act as a heat sink. This helps to ensure uniform treatment and prevent thermal injury to the tissue, such as burns.

The hand piece allows the user to control the placement of fluids because the fluids are delivered directly to the treatment site by the hand piece. The hand piece can then vacuum or suction away the fluids from the treatment site. These two features of the invention help to ensure against heating and burning tissue not intended to be treated, as well as preventing shock hazards to the patient and user.

In a manner similar to RF energy, the radiation sources may transmit microwave energy. In this embodiment, the radiation sources may include one or more microwave antennas. The control unit allows the user to control the microwave parameters, such as power level, cycles, and other parameters, such as selecting pulsed microwaves or continuous microwaves.

The microwave generator may generate a frequency range from about 2 gigahertz to about 20 gigahertz.

In a specific implementation, the radiation sources heat the patient's tissue to about 9 degrees Celsius above the ambient temperature. For example, if the ambient temperature is about 21 degrees Celsius then the radiation sources will heat the patient's tissue to about 30 degrees Celsius. However, in other implementations, the patient's tissue is heated to about 59 degrees Celsius above the ambient temperature. For example, if the ambient temperature is about 21 degrees Celsius then the radiation sources will heat the patient's tissue to about 80 degrees Celsius.

Thus, the patient's tissue (e.g., skin) is typically heated to a temperature range of about 30 degrees Celsius to about 80 degrees Celsius.

A specific implementation of the invention includes a temperature sensor or thermostat 1761 to help regulate the patient's skin temperature. The temperature sensor may be placed at the tip so that the temperature sensor will be near or in contact with the patient's tissue during treatment. For example, the temperature sensor may be placed near or in contact with the radiation sources as shown in FIG. 17.

The temperature sensor is connected via a data line 1764 to the control unit. The temperature sensor detects the temperature of radiation sources, tissue, or both and communicates this information back to the control unit via the data line. This allows the system to ensure that the patient's tissue is being properly heated. For example, if the temperature of the tissue falls below a threshold level then the control unit will increase power to the radiation sources (e.g., microwave antennas). If the temperature of the tissue exceeds a threshold level then the control unit will decrease power to the radiation sources. Thus, the temperature sensor may also function as a safety feature. That is, if the temperature exceeds a maximum threshold value, the control unit may decrease or disconnect power to the radiation sources to prevent the patient's tissue from being burned.

Switch 1740 is coupled to the control unit. Cable 1738 extends from the switch, enters the hand piece and is coupled to one or more radiation sources. The switch is user-operated. The switch allows the user to control the amount of power is supplied to the radiation sources. For example, during a treatment session, the patient may have a particularly sensitive area of skin that they do not want exposed to, for example, RF energy. The switch then allows the user to switch off or decrease the power supply to the radiation sources while power continues to flow to the vacuum source and fluid pump.

In an embodiment, the switch is located at the console as shown in FIG. 17. In other embodiments, the switch is located on the hand piece. In yet another embodiment, the switch may be located between the hand piece and the console.

Although FIG. 17 only shows one switch, other implementations may have multiple switches coupled between the radiation sources and the control unit. For example, there may be two, three, four, five, six, seven, eight, or more than eight switches. These additional switches allow a user to selectively turn on and off individual radiation sources or groups of radiation sources. For example, the radiation sources may include LEDs having varying wavelengths (e.g., blue, red, yellow). Each wavelength may be intended to treat a specific skin condition. A first, second, and third switch may control power to the blue, red, and yellow LEDs, respectively. When a user treats a teenager who only has acne problems, the user may decide to only enable the first switch (i.e., the blue light to treat the acne).

However, the same hand piece can also be used on an adult with both acne and pigmentation problems. In this case, the user would enable both the first and second switches (i.e., blue and red LEDs) to treat the acne and pigmentation.

In an embodiment, multiple switches are used to control different types of radiation sources. For example, the hand piece may include as radiation sources a combination of LEDs, RF electrodes, and microwave antennas. A first, second, and third switch may control power to the LEDs, RF electrodes, and microwave antennas, respectively. The user, depending on the patient's skin condition, may then only enable the first switch for the LEDs, the second switch for the RF electrodes, the third switch for the microwave antennas, or combinations of these.

Furthermore, additional switches may be used to control other components such as the fluid pump, vacuum source, or both. For example, the vacuum source and fluid pump may be controlled by two separate switches. This allows, for example, a "dry" microdermabrasion treatment without fluids. As another example, the user may decide to turn off both the fluid pump and vacuum source to provide only radiation therapy.

A specific implementation of the invention includes negative ion generator 1735. The negative ion generator may further include one or more ion-emitting pins or electrodes for producing negative ions in the air which flows past the electrode. A fan may also be included to direct air past the electrodes.

The negative ion generator may be placed in the console as shown in FIG. 17 or placed in the hand piece. The negative ion generator is optional and may not be included in some implementations of the invention.

The negative ion generator may generate negative ions using, for example, a piezoelectric transformer or a voltage generator. The voltage generator may generate voltages that range from about 1600 volts to about 1700 volts. In other implementations, the voltage generator may generate higher voltages that range from about 6000 volts to about 7000 volts.

The negative ion generator generates negative ions by negatively charging gas molecules, such as oxygen molecules and fine particles in the air. Negative ionization may reduce the concentration of airborne contaminates such as pollen, dust, dust mites, viruses, cigarette smoke, animal dander, odors, and fumes from the breathing zone by binding with these contaminates and causing them to fall to the floor.

These combination skin therapies are further discussed in U.S. patent application Ser. No. 12/197,065, filed Aug. 22, 2008 which is incorporated by reference. This patent application also incorporates by reference U.S. patent application Ser. No. 10/393,682, filed Mar. 19, 2003; Ser. No. 11/562,892, filed Nov. 22, 2006; Ser. No. 29/304,428, filed Feb. 29, 2008; 29/322,102 and 29/322,106, filed Jul. 29, 2008; Ser. Nos. 12/197,047 and 12/197,075, filed Aug. 22, 2008; and U.S. Pat. No. 6,695,853, filed Nov. 21, 2001, and issued Feb. 24, 2004.

A representative flow for treating a patient with a hand piece having an adjustable tip is outlined in steps 1 to 3 below.

1. Determine patient's skin type, condition, desired results, or combinations of these.
2. Adjust distance from tip opening of hand piece to treatment head based on the determination.
3. Apply tip to skin surface.

Although the steps above are listed in a specific order, the steps may take place in any order, as desired and depending on the specific application. There may be additional or other steps, which may replace one or more of the above steps. Certain steps may be repeated. Certain steps may be omitted.

In step 1 of the flow, the user determines the patient's skin type, condition, age, skin sensitivity, desired results, or combinations of these. For example, the user may make the determination by measuring the skin elasticity of a patient using, for example, a cutometer.

In step 2 of the flow, the user adjusts, changes, or alters the distance from the tip opening of the hand piece to the treatment head based on the determination. In a specific implementation, the distance is adjusted by rotating the tip of the hand piece relative to the treatment head.

However, the distance may be adjusted using any of the ideas or concepts presented in this application. For example, the sleeve may be made of two or more interlocking pieces. Changing the distance may include removing one or more of the interlocking pieces, adding one or more interlocking pieces, or both. The interlocking pieces may have the same or different heights. The interlocking pieces may be labeled, color-coded, or both so that the user can distinguish between the different heights of the interlocking pieces.

In step 3 of the flow, the user applies the hand piece or tip opening of the hand piece to the skin surface of the patient. In a specific implementation, suction is provided outside a periphery of the treatment surface through the opening. A portion of the skin surface is drawn through the opening using the suction. The portion of the skin surface drawn is proportional to the distance between the tip opening and the treatment head.

During a treatment session, a patient may be treated with multiple passes or times with the hand piece being progressively adjusted each pass or time. The progressive adjustments may include increasing or decreasing the amount of skin pulled each pass. For example, for a first pass a hand piece may be adjusted so that there is a first distance from a tip opening to a treatment head. For a second pass, the hand piece may be adjusted so that there is a second distance, different from the first distance, from the tip opening to the treatment head.

The same or different portion of skin may be treated for each pass. For example, the user could start with a low setting of the tip so that a small amount of skin is stretched. Once the skin has received this initial stretching, the user could adjust the hand piece to a deeper setting so that a larger amount of skin is stretched. This progressive approach may help to prevent damage to the skin.

FIG. 18 shows a cross section of a hand piece 1805 having a breather hole 1810 and a set of massaging nodes 1815. The breather hole is located on a sleeve 1820 of the adjustable tip and extends through the sleeve, i.e., from an exterior surface of the sleeve to an interior surface of the sleeve. The user, by covering and uncovering the breather hole, can vary the amount of air allowed into the vacuum or flow path and thus vary the amount of suction in the adjustable tip. To increase the amount of suction, the user can use their finger to cover the breather hole which prevents air from flowing through the hole. To decrease the amount of suction, the user can uncover the hole which permits air to flow through the hole.

Although the figure shows the breather hole positioned on the sleeve of the adjustable tip, the breather hole can be located anywhere along the vacuum or flow path of the system. For example, the breather hole may be positioned along vacuum line 202 (FIG. 2). The breather hole may implemented as a valve or any other type of control which allows a user to vary the amount of suction or air in the adjustable tip. In a specific implementation, the breather hole has a diameter of about 1 millimeter.

A representative flow for using a hand piece having a breather hole is outlined in steps 1 to 3 below.

1. Cover breather hole and place adjustable tip of hand piece over patient's skin.
2. Stroke hand piece over patient's skin.
3. Uncover breather hole and lift adjustable tip away from patient's skin.

In step 1 of the flow, the user begins a first or initial stroke of the hand piece over the skin by covering the breather hole. In step 2, while the breather hole is covered, the user runs or strokes the hand piece over the patient's skin. That is, the user completes the first stroke by running the hand piece from a first position on the skin to a second position on the skin.

In step 3, after the first stroke is completed, the user uncovers the breather hole. This allows air into the adjustable tip. The flow of air into the tip decreases the amount of suction in the tip. This allows the tip to be lifted away from the skin without excessively pulling the skin which can damage the skin, cause the patient discomfort, or both. The user can then reposition the tip at a third position on the skin, cover the breather hole, and begin a second or subsequent stroke of the hand piece over the skin. The breather hole is optional and is not included in some implementations of the invention.

In this specific implementation, the massaging nodes are integrally formed with the sleeve of the tip and extend from an edge 1825 or perimeter or circumference of the sleeve in a direction perpendicular to a surface of the treatment head. The massaging nodes surround or at least partially surround the treatment head or tip opening. In another implementation, the massaging nodes are instead or additionally formed on the treatment head. For example, a first portion of the treatment head may include abrasive particles (e.g., diamond particles). A second portion of the treatment head may include massaging nodes. The second portion may surround or at least partially surround the first portion. The first portion may surround or at least partially surround the second portion.

There can be any number of massaging nodes (e.g., 4, 5, 6, 7, 8, 9, 10, or more than 10 massaging nodes). The massaging nodes may be referred to as lumps, ridges, fingers, projections, rounded protrusions, rounded mounds, or bumps (i.e., a relatively abrupt convexity or protuberance on a surface). The massaging nodes may be made of a rigid material (e.g., plastic) or a compliant material such as an elastomeric material. The nodes may be made of rubber or silicon. These massaging nodes can be used to provide a kneading and massaging effect as the hand piece is being run across the patient's skin. The massaging nodes are optional and are not included in some implementations of the invention. Hand pieces without massaging nodes may be able to form a tighter seal against the patient's skin.

FIG. 20 shows a side view of a hand piece 2005 having a motor 2015 or servo to adjust the position of a treatment head 2020 relative to a tip opening 2025. In this specific implementation, the motor is connected to a sleeve 2030 of the hand piece, but may instead or additionally be connected to the treatment head. An electrical connection (not shown) connects the motor to a power supply.

In a specific implementation, the motor causes the treatment head and tip opening to reciprocate (e.g., pulse or modulate) relative to each other, i.e., rapidly alternate between a first distance from the treatment head to the tip opening and a second distance from the treatment head to the tip opening. The frequency of the reciprocation may range from about 25 cycles per minute to about 500 cycles per minute where a cycle is a movement from a first position to a second position and then back to the first position of the treatment head relative to the tip opening—i.e., a movement from a shallow setting to a deep setting to a shallow setting.

In this specific implementation, the motor allows for a treatment setting where the hand piece alternates between settings. This allows for real-time merging of the benefits of both shallow and deep settings through pulsation rather than multiple passes at different depth settings. The reciprocating action or massaging action can have various therapeutic benefits. For example, the reciprocating action can help to break down cellulite and adipose tissue.

FIGS. A-FF in the appendix show various implementations of a hand piece of the skin treatment system. Any one of these hand pieces may be used for treating the skin. In a specific implementation, a hand piece delivers a combination of therapies simultaneously including body polishing, vacuum massage, and infusion or Dermalinfusion™. This combination of therapies can address the underlying cellular processes that bring about skin imperfections in many areas of the body. Each hand piece includes an adjustable-depth tip, allowing the operator to treat a broad range of skin types and conditions associated with the body. High settings allow for treating cellulite, restoring elasticity, and providing deep lymphatic massage. Lower settings allow for treating stretch marks, rough skin, and acne. FIG. GG in the appendix shows a brochure describing some features of a specific implementation of the skin treatment system.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method of treating skin comprising:
changing a distance between an opening of a treatment tip to a treatment surface, wherein the treatment surface faces toward the opening,
the treatment surface is within the opening and skin to be placed against the opening for treatment is outside the opening,
a first length of the opening is greater than a second length of the treatment surface,
there are a plurality of adjustable settings that alter the distance between the treatment surface and the opening, and for each of the settings, the treatment surface does not extend past the opening to outside the opening, and the distance between the treatment surface and the opening is greater than zero;
applying the treatment tip to a skin surface;
providing suction outside a periphery of the treatment surface through the opening; and
drawing a portion of the skin surface through the opening toward the treatment surface using the suction, wherein the portion of the skin surface drawn is proportional to the distance.

2. The method of claim 1 wherein the distance is changeable within a range from about 4 millimeters to about 15 millimeters.

3. The method of claim 1 wherein the opening of the treatment tip is provided by a sleeve having a plurality of interlocking sleeve pieces and the changing a distance between an opening of a treatment tip to a treatment surface comprises removing a first interlocking sleeve piece.

4. The method of claim 1 further comprising:
providing a fluid to the portion of the skin surface using the suction, wherein the fluid does not exit the opening.

5. The method of claim 4 wherein the treatment surface comprises no abrasive particles.

6. The method of claim 5 wherein the second structure is removably coupled to a third structure, the third structure can be rotated about an axis of the first structure, a first O-ring is between the first and second structures, and a second O-ring between the second and third structures.

7. The method of claim 1 wherein the treatment surface is provided by a first treatment head having a first thickness and the changing a distance between an opening of a treatment tip to a treatment surface comprises replacing the first treatment head with a second treatment head having a second thickness, different from the first thickness.

8. The method of claim 1 wherein the skin surface comprises a wart caused by a human papillomavirus (HPV) infection, and the method further comprises:
moving the treatment tip over the wart and, using abrasive particles of the treatment surface, removing a layer of dead skin on the wart; and
providing a treatment liquid via the treatment tip to tissue below the layer of dead skin.

9. The method of claim 1 wherein the skin surface comprises hyperkeratotic tissue, and the method further comprises:
moving the treatment tip over the hyperkeratotic tissue and, using abrasive particles of the treatment surface, removing at least a layer of the hyperkeratotic tissue; and
providing a treatment liquid via the treatment tip to tissue below the layer of hyperkeratotic tissue.

10. The method of claim 9 wherein the hyperkeratotic tissue comprises a callus.

11. The method of claim 1 wherein the treatment tip is coupled to a tubular fluid passageway that extends from a proximal end toward a distal end of a hand piece.

12. The method of claim 1 wherein the treatment tip comprises an adjusting collar rotatable about the treatment surface throughout the plurality of adjustable settings, thereby adjusting the distance between the treatment surface and the opening.

13. The method of claim 12 wherein for a first setting of the plurality of adjustable settings, a minimum distance that can separate the opening and the treatment surface is such that the treatment surface within the opening does not extend past the opening and the distance between the treatment surface and opening is greater than zero.

14. The method of claim 12 wherein the treatment tip comprises an indexing assembly for releasably retaining the adjusting collar in a selected angular position, the selected angular position can be overcome by a user applying torque to the adjusting collar, the indexing assembly comprising a ball detent, and a ball of the ball detent is urged via a spring into a plurality of detents formed on treatment tip.

15. The method of claim 1 wherein for a first setting of the plurality of adjustable settings, a minimum distance that can separate the opening and the treatment surface is such that the treatment surface within the opening does not extend past the opening and the distance between the treatment surface and opening is greater than zero.

16. A method of treating skin comprising:
    changing a distance between an opening of a treatment tip to a treatment surface, wherein the treatment surface coupled to a first structure,
    a second structure is coupled to the first structure and comprises a first end having the opening, wherein the treatment surface is within the opening, skin to be placed against the opening for treatment is outside the opening, and a first length of the opening is greater than a second length of the treatment surface,
    the second structure is movable relative to the first structure, thereby allowing altering of a position of the treatment surface relative to the opening within the opening, and the treatment surface does not extend past the opening to outside the opening, and
    a stop member is directly coupled to the first structure, and the stop member prevents movement of the second structure into a position such that the treatment surface extends outside of the opening;
    applying the treatment tip to a skin surface;
    providing suction outside a periphery of the treatment surface through the opening; and
    drawing a portion of the skin surface through the opening toward the treatment surface using the suction, wherein the portion of the skin surface drawn is proportional to the distance.

17. The method of claim 16 wherein the stop member extends longitudinally and radially along a longitudinal axis of the first structure, the stop member comprising a first end and a second end of the stop member,
    when the second structure is moved in a first direction along the longitudinal axis of the first structure, the first end prevents the second structure from being moved beyond the first end in the first direction into a position such that the treatment surface extends outside of the opening, and
    when the second structure is moved in a second direction that is opposite the first direction, the second end prevents the second structure from being moved beyond the second end in the second direction.

18. The method of claim 16 wherein the second structure is rotatable about an axis of the first structure.

19. The method of claim 16 wherein the first structure comprises a tubular passageway, and a flow path of a fluid comprising a liquid is from proximal end to a distal end of the tubular passageway to the treatment surface, away from a center of the treatment surface, and into an annular space surrounding at least a portion of the tubular passageway.

20. The method of claim 16 wherein the treatment surface comprises no abrasive particles.

* * * * *